US008962031B2

(12) United States Patent
Mahmoudi et al.

(10) Patent No.: US 8,962,031 B2
(45) Date of Patent: Feb. 24, 2015

(54) SUPER PARAMAGNETIC IRON OXIDE NANOPARTICLES WITH METALLIC COATINGS AND A METHOD OF SYNTHESIZING THE SAME

(71) Applicants: Morteza Mahmoudi, Tehran (IR); Mohammad Ali Shokrgozar, Tehran (IR); Pasteur Institute of Iran, Tehran (IR)

(72) Inventors: Morteza Mahmoudi, Tehran (IR); Mohammad Ali Shokrgozar, Terhan (IR)

(*) Notice: Subject to any disclaimer, the term of this patent is extended or adjusted under 35 U.S.C. 154(b) by 0 days.

(21) Appl. No.: 13/771,479

(22) Filed: Feb. 20, 2013

(65) Prior Publication Data

US 2014/0234429 A1    Aug. 21, 2014

(51) Int. Cl.
 *A61K 9/14* (2006.01)
 *A61K 9/16* (2006.01)
 *B05D 7/00* (2006.01)

(52) U.S. Cl.
 CPC ........................................ *A61K 9/14* (2013.01)
 USPC ........... 424/490; 424/618; 424/649; 427/2.14

(58) Field of Classification Search
 None
 See application file for complete search history.

(56) References Cited

U.S. PATENT DOCUMENTS 7,175,912 B2 * 2/2007 Cui et al. ...................... 428/403
2011/0206619 A1 * 8/2011 Mahmoudi et al. ........ 424/9.323

OTHER PUBLICATIONS

Taylor et al. Magnetic Nanoparticles and a Magnetic Field for the Rapid Removal of Device Related Infections. (Apr. 2011).*
Yongdong et al. Multifunctional Nanoparticles as Coupled Contrast Agents. Jul. 2010).*
Gordon et al. Silver Coordination Polymers for Prevention of Implant Infection: Thiol Interaction, Impact on Respiratory Chain Enzymes, and Hydroxyl Radical Induction (Jul. 2010).*
Mahmoudi et al. Silver-Coated Engineered Magnetic Nanoparticles Are Promising for the Success in the Fight Against Antibacterial Resistance Threat (Mar. 7, 2012).*

* cited by examiner

*Primary Examiner* — Scott Long
*Assistant Examiner* — Sarah Alawadi
(74) *Attorney, Agent, or Firm* — Barry Choobin; Patent 360 LLC

(57) ABSTRACT

The various embodiments herein provide super paramagnetic iron oxide nanoparticles (SPIONs). The SPIONs have a plurality of metallic coatings and plurality of polymeric gaps. The embodiments herein also provide a method of synthesizing the SPIONs with metallic rings and polymeric gaps. The metallic coatings form a ring like structure on the outer surface of the SPION. The SPION has a size of 13 nm. The ring has a thickness of 2-3 nm. The rings are one or more in number. The polymeric gaps have a thickness of 3-5 nm. The polymeric gaps are one or more in number. The method involves mixing the SPIONs with a plurality of polymers and then forming a metallic ring on the outer surface of the SPIONs. The SPIONs have anti-bacterial properties and stop a growth of bacterial biofilms. The SPIONs also have SERS properties.

13 Claims, 33 Drawing Sheets

SUPER PARAMAGNETIC IRON OXIDE NANOPARTICLES WITH METALLIC COATINGS AND A METHOD OF SYNTHESIZING THE SAME

BACKGROUND

1. Technical Field

The embodiments herein generally relate to engineered multimodal nanoparticles with antibacterial effects for theranosis applications. The embodiments herein particularly relate to the anti-bacterial agents with an ability to eradicate a growth of bacteria and bacterial biofilms. The embodiments herein more particularly relate to super paramagnetic iron oxide nanoparticles (SPIONs) having metallic coatings with a plurality of polymeric gaps and a method of synthesizing the SPIONs having metallic outer coatings with polymeric gaps.

2. Description of the Related Art

Antibiotics have been long known as 'Miraculous Drugs' for curing the various fatal infectious diseases. The Antibiotics have been excessively used even without taking a prescription by a doctor. This has lead to an inappropriate and a disproportionate use of the antibiotics. The inappropriate and disproportionate use of antibiotics or antibacterial agents has led to a rapid increase in a prevalence of drug-resistant microorganisms. For example, the use of penicillin drug in the treatment of infections caused by the microorganism *Staphylococcus aureus* in humans, animals and plants has led to a development of a resistant variety against the drug.

The most catastrophic effect of antibiotics resistance is the emergence of new bacterial strains which are simultaneously resistant to the numerous antibiotics. The new infections caused by these multi-drug resistant pathogens dramatically aggravate the clinical complications. The multi-drug resistant pathogens cause a higher risk of serious diseases that are readily treated. The multi-drug resistant pathogens require a longer hospital stays for the patients that amounts to a considerable greater expense for the society. In the most severe circumstances, an incompetence of the employed antibiotics to the newly developed dangerous pathogens can cause an uncontrolled epidemics of the bacterial diseases that can no longer be treated.

The pathogenic infections that are associated with the biomaterials are another critical issue. The average life expectancy in a human society has been gradually increasing. The increase in the life expectancy in the human society results in higher demands for the replacement of organs or tissues by the biomaterials especially in the elderly people. Consequently the use of biomaterial implants, such as artificial tissues, is on an increase extensively. The pathogenic infections are initiated immediately after a surgery by a perioperative bacterial contamination of a graft surface during an implantation of these artificial tissues. The infection also starts during the hospitalization or through the hematogenous spreading of a bacteria from the infections elsewhere in the body. In general, *Staphylococcus epidermidis* and *Staphylococcus aureus* are the most frequently isolated pathogens from the infected biomaterial implants. Approximately 50% of the infections associated with catheters, artificial joints and heart valves are caused by *Staphylococcus epidermidis* whereas *Staphylococcus aureus* is detected approximately in 23% of the infections associated with the prosthetic joints. *Staphylococcus epidermidis* and *Staphylococcus aureus* often protect themselves against the antibiotics and the host immune system by producing a matrix of the exo-polymeric substances that embed the organisms in a matrix. The matrix is impenetrable for most of the antibiotics and immune cells. Accordingly the alternative drugs should have the capability to infiltrate the biofilm in order to increase the efficacy of the antibiotics.

As the social and economic impacts of the nano technological developments is being recognized nowadays, the nanotechnology has become a prime interest in public. However, there are still several unknown aspects of the widespread application of the nano sciences in the fields of human life, novel materials manufacturing, electronics, cosmetics, pharmaceutics and medicine. During the last decade an application of the nano-materials in medicine has significantly increased. This increases the hopes for employing the nanoparticles as the alternative antibiotic agents. The silver nanoparticles are well recognized as the promising antimicrobial agents among the various types of nanoparticles. However there are two major shortcomings with these particles. Firstly the silver nanoparticles have a toxic effect on the human cells and secondly the silver nanoparticles have a low yield for a penetration through the bacterial biofilms.

Hence there is a need to develop a novel group of engineered multimodal nanoparticles with antibacterial effects such as antibacterial agents for theranosis applications. Further there is a need to develop the antibacterial agents with an ability to eradicate a growth of the bacterial biofilms and to avoid a growth of a bacteria. Also there is a need to develop a group of anti-bacterial agents with promising profiles for successfully fighting an Antibacterial Resistance Threat.

The above mentioned shortcomings, disadvantages and problems are addressed herein and which will be understood by reading and studying the following specification.

OBJECTIVES OF THE EMBODIMENTS HEREIN

The primary objective of the embodiments herein is to develop engineered multimodal nanoparticles with antibacterial effects such as antibacterial agents for theranosis applications.

Another objective of the embodiments herein is to develop a class of newly developed anti-bacterial agents comprising super paramagnetic iron oxide nanoparticles (SPIONs) with metallic coatings and polymeric gaps.

Yet another objective of the embodiments herein is to provide a method of synthesizing the super paramagnetic iron oxide nanoparticles (SPIONs) with a plurality metallic coatings and a plurality of polymeric gaps.

Yet another objective of the embodiments herein is to provide anti bacterial agents that have a property of eradicating the growth of bacterial biofilms.

Yet another objective of the embodiments herein is to provide super paramagnetic iron oxide nanoparticles (SPIONs) with gold and silver metal coatings.

Yet another objective of the embodiments herein is to provide super paramagnetic iron oxide nanoparticles (SPIONs) forming the promising profiles for successfully fighting against Antibacterial Resistance Threat.

Yet another objective of the embodiments herein is to provide super paramagnetic iron oxide nanoparticles (SPIONs) that are completely compatible with the biological cells.

Yet another objective of the embodiments herein is to provide super paramagnetic iron oxide nanoparticles (SPIONs) with anti-bacterial property due to the presence of silver as a shell.

Yet another objective of the embodiments herein is to provide super paramagnetic iron oxide nanoparticles (SPIONs) with Surface Enhanced Raman scattering (SERS) properties for utilizing in molecular imaging and sensing applications.

Yet another objective of the embodiments herein is to provide super paramagnetic iron oxide nanoparticles (SPIONs) that are employed as pre-programmed smart reagents for a single-DNA detection of the pathogens having a promising impact for tackling the threats associated with the antibiotics resistance.

These and other objects and advantages of the embodiments herein will become readily apparent from the following detailed description taken in conjunction with the accompanying drawings.

SUMMARY

The embodiments herein provide an engineered multimodal nanoparticle with anti-bacterial effect and theranosis application and a method of synthesizing the nanoparticles.

According to one embodiment herein, the engineered multimodal nanoparticle with anti-bacterial effect and theranosis application comprises a super paramagnetic iron oxide nanoparticle (SPION) with at least one coating and at least one gap. The coating is made up of a metal. The gap is made up of a plurality of polymeric molecules. The metal is selected from a group consisting of a silver, a gold and a combination thereof. The coating is two in number. The coating has a thickness of 2-3 nm. The plurality of polymeric molecules are selected from a group consisting of carboxylated-dextran compound, ethanediyl bis(isonicotinate) compound, b is 2-((4-pyridinylcarbonyl)oxy)ethyl disulfide compound, molecules of poly-L-histidine compound and a combination thereof. The gap is two in number. The gap has a thickness of 3-5 nm. The nanoparticle stops a growth of a bacterial biofilm. The nanoparticle is compatible with biological cells. The nanoparticle has a Surface Enhanced Raman Scattering (SERS) Properties.

According to one embodiment herein, a method for synthesizing an engineered multimodal nanoparticle with anti-bacterial effect and theranosis application comprises mixing a solution of SPIONs with a solution of a polysaccharide at a room temperature for a predetermined time to obtain the SPIONs with a coating of the polysaccharide. The predetermined time is 72 hours. The obtained SPIONs are mixed with a solution of a preset compound for a time period of 20 minutes to obtain the SPIONs with a further coating of the preset compound.

The obtained SPIONs are mixed with a metal salt solution for a duration of 20 minutes to obtain the SPIONs with accumulated metal ions on their surface.

The obtained SPIONs are then separated from the metal salt solution. The obtained SPIONs are separated using a Magnetic-Activated Cell Sorting system (MACS).

The obtained SPIONs are added with a reducing agent to reduce the accumulated metal ions to further obtain the SPIONs with a metal coating on an outer surface having a polymeric gap. The polymeric gap is situated in between the metal coating and the SPION surface. The obtained SPIONs are collected.

The polysaccharide is carboxylated dextran. The preset compound is ethanediyl bis(isonicotinate). The metal salt solution is silver nitride. The reducing agent is sodium borohydride.

The metal coating is a silver coating and the metal coating is 2-3 nm in thickness. The polymeric gap is made up of molecules of the polysaccharide and the preset compound. The polymeric gap is made up of molecules of a carboxylated dextran and molecules of an ethanediyl bis(isonicotinate). The polymeric gap is 3-5 nm in thickness.

According to an embodiment herein, a method of synthesizing an engineered multimodal nanoparticle with anti-bacterial effect and theranosis application comprises dispersing gold coated SPIONs in a solution of a disulphide compound. The solution is further mixed for duration of 5 hrs. The gold coated SPIONs are then collected by MACS system. The collected gold coated SPIONs are mixed with a metal salt solution. The metal ions get accumulated on the surface of the gold coated SPIONs. The gold coated SPIONs are further added with a reducing agent to reduce the metal ions to obtain the SPIONs with a plurality of metallic coatings and a plurality of polymeric gaps.

The disulphide compound is bis 2-((4-pyridinylcarbonyl)oxy)ethyl disulfide. The salt solution is silver nitride. The reducing agent is sodium borohydride. The metallic coatings are two in number. The metallic coatings have a thickness of 2-3 nm. The metallic coatings include a gold coating and a silver coating. The polymeric gaps are two in number. The polymeric gaps have a thickness of 3-5 nm. The polymeric gaps are made up of a plurality of molecules of polymers. The polymers are selected from a group consisting of carboxylated-dextran, ethanediyl bis(isonicotinate), h is 2-((4-pyridinylcarbonyl)oxy)ethyl disulfide, poly-L-histidine and a combination thereof.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
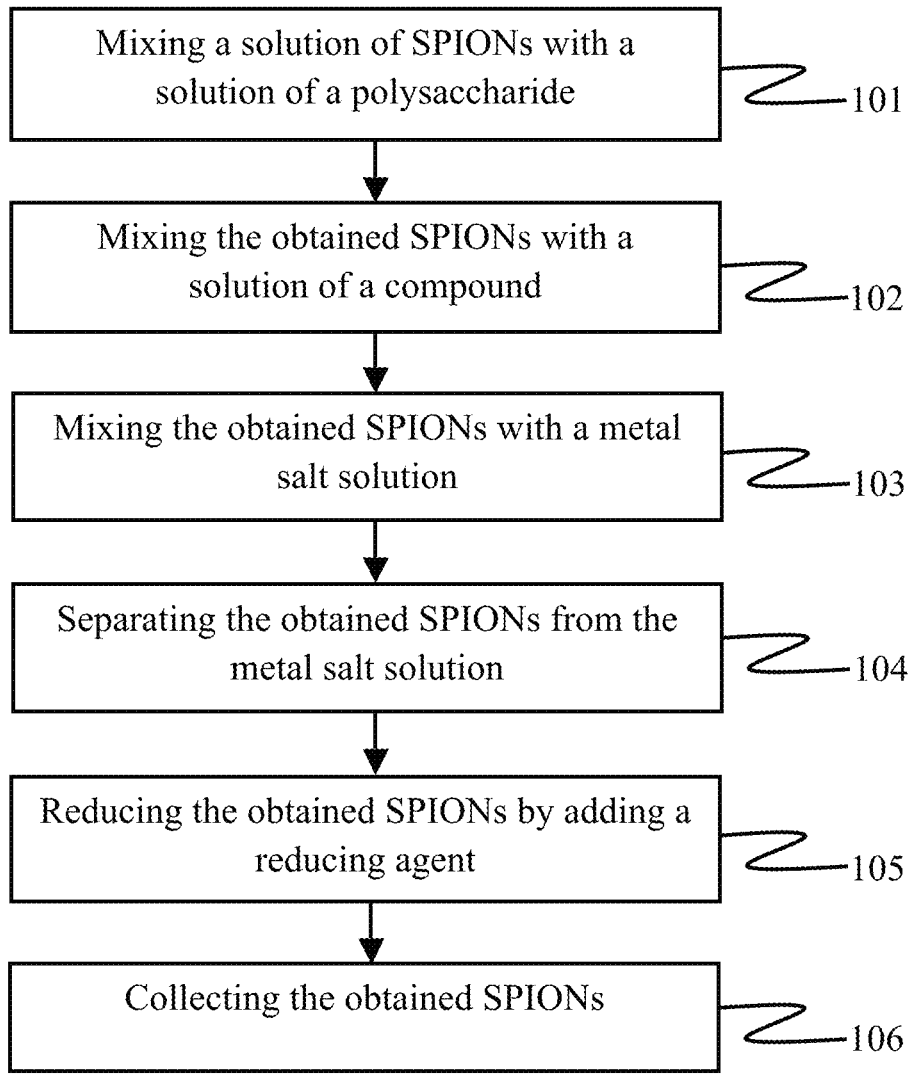
FIG. 1 shows a flow chart illustrating the various steps involved in the synthesis of the super paramagnetic iron oxide nanoparticles (SPIONs) with a metallic coating, according to an embodiment herein.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The embodiments herein provide an engineered multimodal nanoparticle with anti-bacterial effect and theranosis application and a method of synthesizing the nanoparticles.

According to one embodiment herein, the engineered multimodal nanoparticle with anti-bacterial effect and theranosis application comprises a super paramagnetic iron oxide nanoparticle (SPION) with at least one coating and at least one gap. The coating is made up of a metal. The gap is made up of a plurality of polymeric molecules. The metal is selected from a group consisting of a silver, a gold and a combination thereof. The coating is two in number. The coating has a thickness of 2-3 nm. The plurality of polymeric molecules are selected from a group consisting of carboxylated-dextran compound, ethanediyl bis(isonicotinate) compound, b is 2-((4-pyridinylcarbonyl)oxy)ethyl disulfide compound, molecules of poly-L-histidine compound and a combination thereof. The gap is two in number. The gap has a thickness of 3-5 nm. The nanoparticle stops a growth of a bacterial biofilm. The nanoparticle is compatible with biological cells. The nanoparticle has a Surface Enhanced Raman Scattering (SERS) Properties.

According to one embodiment herein, a method for synthesizing an engineered multimodal nanoparticle with antibacterial effect and theranosis application comprises mixing a solution of SPIONs with a solution of a polysaccharide at a room temperature for a predetermined time to obtain the SPIONs with a coating of the polysaccharide. The predetermined time is 72 hours. The obtained SPIONs are mixed with a solution of a preset compound for a time period of 20 minutes to obtain the SPIONs with a further coating of the preset compound.

The obtained SPIONs are mixed with a metal salt solution for a duration of 20 minutes to obtain the SPIONs with accumulated metal ions on their surface.

The obtained SPIONs are then separated from the metal salt solution. The obtained SPIONs are separated using a Magnetic-Activated Cell Sorting system (MACS).

The obtained SPIONs are added with a reducing agent to reduce the accumulated metal ions to further obtain the SPIONs with a metal coating on an outer surface having a polymeric gap. The polymeric gap is situated in between the metal coating and the SPION surface. The obtained SPIONs are collected.

The polysaccharide is carboxylated dextran. The preset compound is ethanediyl bis(isonicotinate). The metal salt solution is silver nitride. The reducing agent is sodium borohydride.

The metal coating is a silver coating and the metal coating is 2-3 nm in thickness. The polymeric gap is made up of molecules of the polysaccharide and the preset compound. The polymeric gap is made up of molecules of a carboxylated dextran and molecules of an ethanediyl bis(isonicotinate). The polymeric gap is 3-5 nm in thickness.

According to an embodiment herein, a method of synthesizing an engineered multimodal nanoparticle with anti-bacterial effect and theranosis application comprises dispersing gold coated SPIONs in a solution of a disulphide compound. The solution is further mixed for duration of 5 hrs. The gold coated SPIONs are then collected by MACS system. The collected gold coated SPIONs are mixed with a metal salt solution. The metal ions get accumulated on the surface of the gold coated SPIONs. The gold coated SPIONs are further added with a reducing agent to reduce the metal ions to obtain the SPIONs with a plurality of metallic coatings and a plurality of polymeric gaps.

The disulphide compound is bis 2-((4-pyridinylcarbonyl)oxy)ethyl disulfide. The salt solution is silver nitride. The reducing agent is sodium borohydride. The metallic coatings are two in number. The metallic coatings have a thickness of 2-3 nm. The metallic coatings include a gold coating and a silver coating. The polymeric gaps are two in number. The polymeric gaps have a thickness of 3-5 nm. The polymeric gaps are made up of a plurality of molecules of polymers. The polymers are selected from a group consisting of carboxylated-dextran, ethanediyl bis(isonicotinate), h is 2-((4-pyridinylcarbonyl)oxy)ethyl disulfide, poly-L-histidine and a combination thereof.

The various embodiments herein provide superparamagnetic iron oxide nanoparticles with metallic coatings. The term "superparamagnetic iron oxide nanoparticles" and "SPIONs" are used interchangeably in the foregoing detailed description. The metallic coatings are made up of a metal. The metal is any one of gold or silver or both. The metallic coatings are in the form of rings. The SPION and the coatings have a gap in between their intermediate surfaces. The gap is made up of polymeric molecules. This novel class of SPIONs with the ultrathin metallic rings and polymeric gaps exhibit the strong anti-microbial characteristics against a bacteria while they maintain a remarkable compatibility with the biological cells. The metallic rings are selected from a group consisting of a gold ring and a silver ring. The rings has a thickness of 1-2 nm.

According to one embodiment herein, the SPIONs with an ultrathin silver ring coating with polymeric gaps are provided. The SPIONS with silver coating exhibits strong antimicrobial characteristics against bacteria while maintaining a remarkable compatibility with the cells. The silver ring has a thickness of 1-2 nm.

According to an embodiment herein, the SPIONs with an ultrathin gold ring coating with polymeric gaps are provided. The SPIONS with gold ring exhibit the strong antimicrobial characteristics against bacteria while maintaining a remarkable compatibility with the cells. The silver ring a thickness of 1-2 nm.

According to an embodiment herein, the SPIONs with ultrathin plurality of coatings and plurality of gaps are provided. The plurality of coatings is in the form of rings. The plurality of coatings includes a gold ring and a silver ring. The rings have a thickness of 1-2 nm. The SPIONs with a plurality of coatings and a plurality of gaps have a remarkable antibacterial property. The SPIONs with a plurality of coatings and gaps are compatible with the biological cells. The polymeric gaps are made up of the molecules of polymers. This novel class of SPIONs is potentially used as multimodal antibacterial agents.

According to an embodiment herein, the SPIONs with ultrathin gold ring followed by a silver ring with double polymeric gaps are provided. The first polymeric gap is situated between the SPION core and the first ring. The second polymeric gap is arranged between the first ring and the second ring. The first ring is a gold ring and the second ring is a silver ring. The polymeric gaps are made up of molecules of polymers. The SPIONs with an ultrathin gold ring followed by a silver ring with double polymeric gaps have an antibacterial property.

According to the embodiments herein, the SPIONs are able to deeply penetrate into the bacterial biofilms due to their magnetic core when an external magnetic field is applied resulting in a high therapeutic index against *Staphylococcus epidermidis* and *Staphylococcus aureus* infections.

According to one embodiment herein, a super paramagnetic iron oxide nanoparticle (SPION) with metallic coatings is provided. The SPION with metallic coatings comprises a core, one or more coatings and one or more gaps. The core is made up of a super paramagnetic iron oxide nanoparticle (SPION). The coatings are made up of a metal. The metal is selected from a group consisting of silver, gold and a combination thereof. The coating is one in number according to an embodiment herein. The coating is two in number according to another embodiment herein. The coating is 2-3 nm in thickness. The gaps are made up of a plurality of polymeric molecules. The plurality of polymeric molecules are selected from a group consisting of carboxylated-dextran compound, ethanediyl bis(isonicotinate) compound, b is 2-((4-pyridinylcarbonyl)oxy)ethyl disulfide compound, poly-L-histidine compound and a combination thereof. The gap is one in number according to one embodiment herein. The gaps are two in number according to another embodiment herein. The gap has a thickness of 3-5 nm.

The nanoparticle has an anti-bacterial property. The nanoparticle stops a growth of a bacterial biofilm. The nanoparticle is compatible with the biological cells. The nanoparticle exhibits the Surface Enhanced Raman Scattering (SERS) Properties.

According to an embodiment, a method for synthesizing a super paramagnetic iron oxide nanoparticle (SPION) with a metallic coating is provided. The method of synthesizing a super paramagnetic iron oxide nanoparticle (SPION) with a metallic coating comprises mixing a solution of SPIONs with a solution of a polysaccharide at a room temperature for a predetermined time to obtain the SPIONs with a coating of the polysaccharide. The polysaccharide is a carboxylated dextran. The predetermined time is 72 hours. The obtained SPIONs are mixed with a solution of a preset compound for a time period of 20 minutes to obtain SPIONs with a further coating of the preset compound. The preset compound is ethanediyl bis(isonicotinate). Further the obtained SPIONs are mixed with a metal salt solution for a duration of 20 minutes to obtain the SPIONs with the accumulated metal ions on their surface. The metal salt solution is a silver nitride solution. The obtained SPIONs are then separated from the metal salt solution. The obtained SPIONs are separated using a Magnetic-Activated Cell Sorting system (MACS). The obtained SPIONs are added with a reducing agent to reduce the accumulated metal ions to obtain the SPIONs with a metal coating on an outer surface having a polymeric gap. The polymeric gap is situated in between the metal coating and the SPION surface. The reducing agent is sodium borohydride. The obtained SPIONs are collected. The metal coating is a silver coating and the metal coating has a thickness of 2-3 nm. The polymeric gap is made up of molecules of the polysaccharide and the preset compound. The polymeric gap has a thickness of 3-5 nm.

According to an embodiment herein, a method of synthesizing super paramagnetic iron oxide nanoparticles (SPIONs) with the metallic coatings is provided. The metallic coating has gold and silver coatings. The metallic coatings are two in number according to an embodiment herein. The plurality of polymeric gaps are two in number. The method of synthesizing super paramagnetic iron oxide nanoparticles (SPIONs) with the metallic coatings comprises treating a surface of gold coated SPIONs to obtain the SPIONs with a plurality of metallic coatings and a plurality of polymeric gaps. The step of treating the surface of the gold coated SPIONs further comprises dispersing the gold coated SPIONs in a solution of a disulphide compound. The disulphide compound is his 2-((4-pyridinylcarbonyl)oxy)ethyl disulfide. The solution is further mixed for a duration of 5 hrs. The gold coated SPIONs are collected by MACS system. The collected gold coated SPIONs are mixed with a metal salt solution. The metal ions get accumulated on the surface of the gold coated SPIONs. The metal salt solution is a silver nitride solution. The gold coated SPIONs are further added with a reducing agent to reduce the metal ions to obtain the SPIONs with a plurality of metallic coatings and a plurality of polymeric gaps. The reducing agent is sodium borohydride. The metallic coatings are two in number. The metallic coating has a thickness of 2-3 nm. The metallic coatings include a gold coating and a silver coating. The polymeric gaps are two in number. The polymeric gaps have a thickness of 3-5 nm. The polymeric gaps are made up of a plurality of molecules of polymers. The polymers are selected from a group consisting of carboxylated-dextran, ethanediyl bis(isonicotinate), h is 2-((4-pyridinylcarbonyl)oxy)ethyl disulfide, poly-L-histidine and a combination thereof.

The formation of the SPIONs, provided in the em embodiments herein, strongly enhances the anti microbial activities of silver, The SPIONs according to the embodiments herein enhance the antimicrobial activity by not only a through up regulation of Reactive Oxygen Species (ROS) production in bacteria but also by the deep penetration of these SPIONs within the bacterial biofilms using an external magnetic field. The SPIONs according to the embodiments herein are engineered magnetic nanoparticles that do not cause toxicity to the human cells. Hence these SPIONs form an efficient antimicrobial agent in treating the pathogens and infections. Also the SPIONs according to the embodiments herein provide the prospective applications in the field of antibacterial agents. Thus these SPIONs also provide a significant consideration by the scientific community in the near future.

According to an embodiment herein, the novel generations of antimicrobial magnetic particles consisting of super paramagnetic cores are designed and synthesized.

FIG. 1 shows a flow chart illustrating the various steps involved in the synthesis of the super paramagnetic iron oxide nanoparticles (SPIONs) with a metallic coating, according to an embodiment herein. With respect to FIG. 1, a solution of SPIONs is mixed with a solution of a polysaccharide (101). The solution of SPIONs is mixed with a solution of a polysaccharide at room temperature for a predetermined time. The predetermined time is 72 hours. The polysaccharide is carboxylated dextran. The obtained SPIONs has a coating of the polysaccharide.

The solution of SPIONs is prepared by dispersing the SPIONs in hexane. The SPIONs are synthesized according to a previously reported procedure. The SPIONs are synthesized with a size of 13 nm. For the synthesis of SPIONs with an average size of 13 nm, the iron-oleate complexes are prepared by reacting a sodium oleate and an iron (III) chloride. The iron-oleate complex and oleic acid are dissolved in 1-octadecene at a room temperature. The reaction mixture is degassed at 80° C. for 2 hrs. The mixture is heated to a reflux temperature at a heating rate of 3° C./minute and then kept for 30 minutes under an inert atmosphere. After the reaction, the container vessel is rapidly cooled down to room temperature, followed by the addition of acetone in order to start the SPIONs precipitation. The SPIONs are separated by a centrifuge and dispersed in hexane.

The Carboxylated-dextran is prepared according to the procedure reported elsewhere. The hydroxyl groups in dextran are oxidized to aldehyde groups using sodium periodate. Briefly, the sodium periodate is dissolved in de-oxygenated DI water and introduced to dextran solution. The dextran has an average molecular weight of 5000. The solution is homogenized for 2 hrs at a room temperature followed by dialyzing with a membrane bag for 4 days. The cyanohydrins intermediate was prepared via an interaction between the obtained solution and the potassium cyanide. Finally, the carboxylic acid groups are created at the terminal units of dextran through the hydrolysis of the obtained cyanohydrins intermediate. The prepared carboxylated dextran is lyophilized and stored at −80° C.

Further, the obtained SPIONs are mixed with a solution of a preset compound (102). The preset compound is ethanediyl bis(isonicotinate). The obtained SPIONs are mixed with a solution of the ethanediyl bis(isonicotinate) compound for a time of 20 minutes. The SPIONs obtained are the SPIONs with a further coating of the ethanediyl bis(isonicotinate) compound.

Then, the obtained SPIONs are mixed with a metal salt solution (103). The obtained SPIONs are mixed with a metal salt solution for a time of 20 minutes. The metal salt solution is silver nitride solution. The obtained SPIONs have accumulated metal ions on their surfaces outside the polysaccharide and the ethanediyl bis(isonicotinate) compound coatings.

The obtained SPIONs are separated from the metal salt solution (104). The obtained SPIONs are separated from the metal salt solution by magnetic-activated cell sorting system (MACS). Then the obtained SPIONs are reduced by adding a reducing agent (105). The reducing agent is sodium borohydride. Finally the obtained SPIONs are collected again using the MACS system (106). The final collected SPIONs have a metal coating on an outer surface having a polymeric gap. The polymeric gap is situated in between the metal coating and the SPION surface. The metal coating is a silver coating. The metal coating has a thickness of 2-3 nm. The polymeric gap is made up of molecules of the polysaccharide and the ethanediyl bis(isonicotinate) compound. The polymeric gap has a thickness of 3-5 nm.

Figure 2:
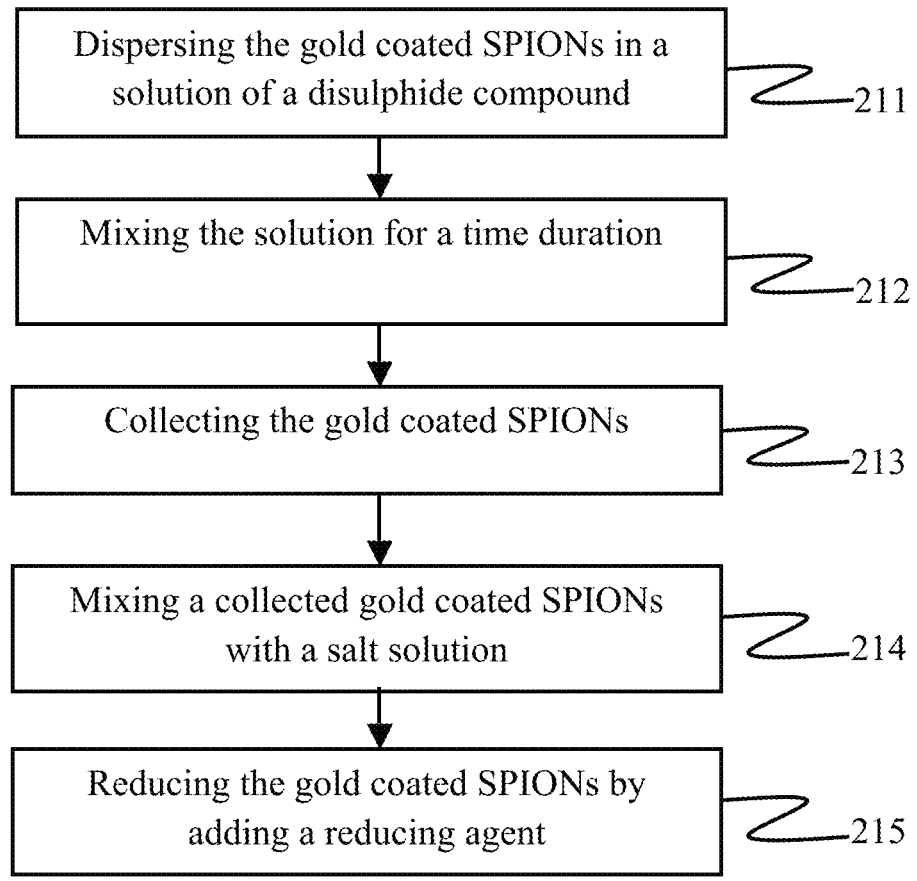
FIG. 2 shows a flow chart illustrating the various steps involved in the synthesis of super paramagnetic iron oxide nanoparticles (SPIONs) with two metallic coatings, according to an embodiment herein.

FIG. 2 shows a flow chart illustrating the various steps involved in the synthesis of super paramagnetic iron oxide nanoparticles (SPIONs) with metallic coatings, according to an embodiment herein. With respect to FIG. 2, gold coated SPIONs are dispersed in a solution of a disulphide compound (211). The disulphide compound is bis 2-((4-pyridinylcarbonyl)oxy)ethyl disulfide. The solution is mixed for a time duration of 5 hrs (212). The obtained gold coated SPIONs are collected by the MACS system (213). The collected SPIONs have a layer of the molecules of the disulphide compound over the gold coating. The collected gold coated SPIONs are mixed with a salt solution (214). The salt solution is silver nitride solution. The gold coated SPIONs are reduced by using a reducing agent (215). The reducing agent is sodium borohydride. The reducing agent reduces the accumulated silver ions on the outer region of the gold coated SPIONs. After the reduction of the SPIONs with the reducing agent, the silver ions form a silver ring coating outside the gold coated SPIONs. Thus the SPIONs with a plurality of metallic coatings and a plurality of polymeric gaps are obtained. The metallic coatings are two in number and the metallic coating has a thickness of 2-3 mm The metallic coatings include a gold coating and a silver coating. The polymeric gaps are two in number and the polymeric gaps have a thickness of 3-5 nm. The polymeric gaps are made up of a plurality of molecules of polymers. The polymers are selected from a group consisting of carboxylated-dextran, ethanediyl bis(isonicotinate), b is 2-((4-pyridinylcarbonyl)oxy)ethyl disulfide, poly-L-histidine and a combination thereof.

Figure 3:
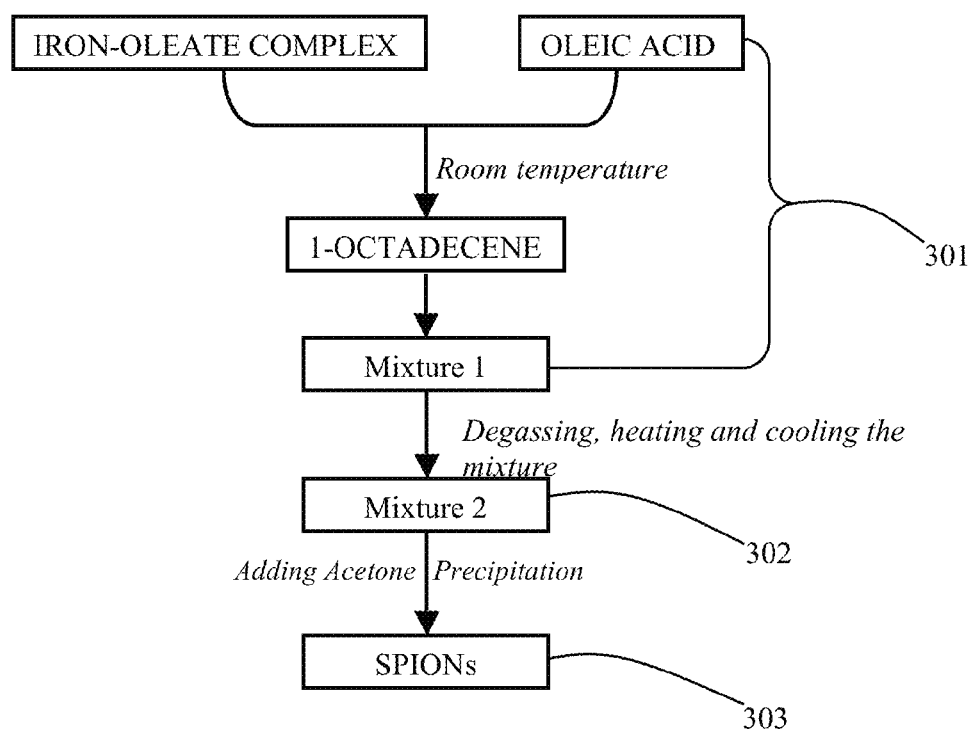
FIG. 3 shows a flow chart illustrating the various steps involved in the synthesis of super paramagnetic iron oxide nanoparticles (SPIONs), according to the embodiments herein.

FIG. 3 shows a flow chart illustrating the various steps involved in the synthesis of super paramagnetic iron oxide nanoparticles (SPIONs), according to the embodiments herein. With respect to FIG. 3, the iron oleate complex and oleic acid are mixed with 1-octadecene at a room temperature to form a Mixture-1 (301). The formed Mixture-1 is degassed at 80° C. for 2 hrs (302). The mixture 1 is then heated to a reflux temperature at a heating rate of 3° C./minute and kept for 30 minutes under an inert atmosphere (302). The Mixture-1 is then rapidly cooled down to a room temperature to form a Mixture-2 (302). The cooling process of Mixture-2 is further followed by an addition of acetone to precipitate out the super paramagnetic iron oxide nanoparticles (303). The precipitates are separated by a centrifugation and dispersed in hexane.

Figure 4:
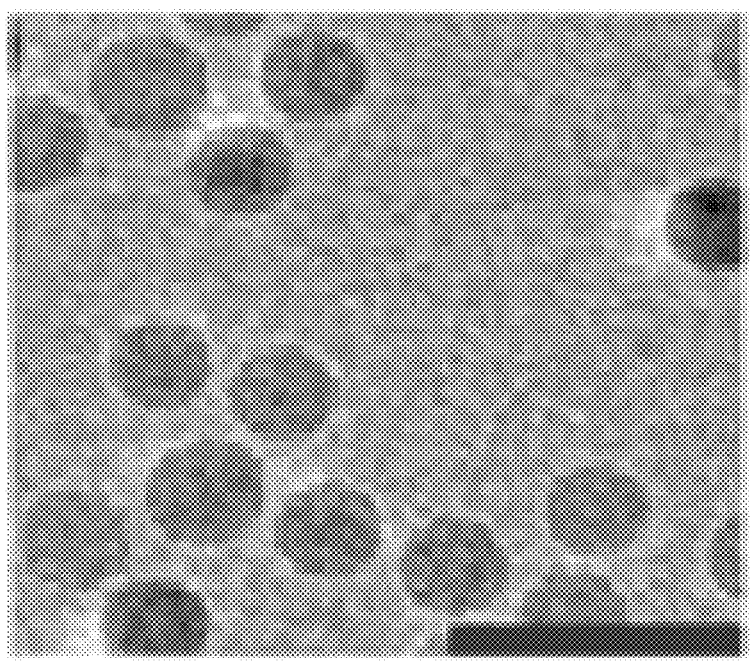
FIG. 4 shows a Transmission Electron Microscopy (TEM) image indicating the synthesized superparamagnetic iron oxide nanoparticles (SPIONs), according an embodiment herein.

FIG. 4 shows a Transmission Electron Microscopy (TEM) image showing the synthesized superparamagnetic iron oxide nanoparticles (SPIONs), according an embodiment herein. With respect to FIG. 4, the synthesized superparamagnetic iron oxide nanoparticles are visible. The iron oxide nanoparticles are spherical in shape.

Figure 5:
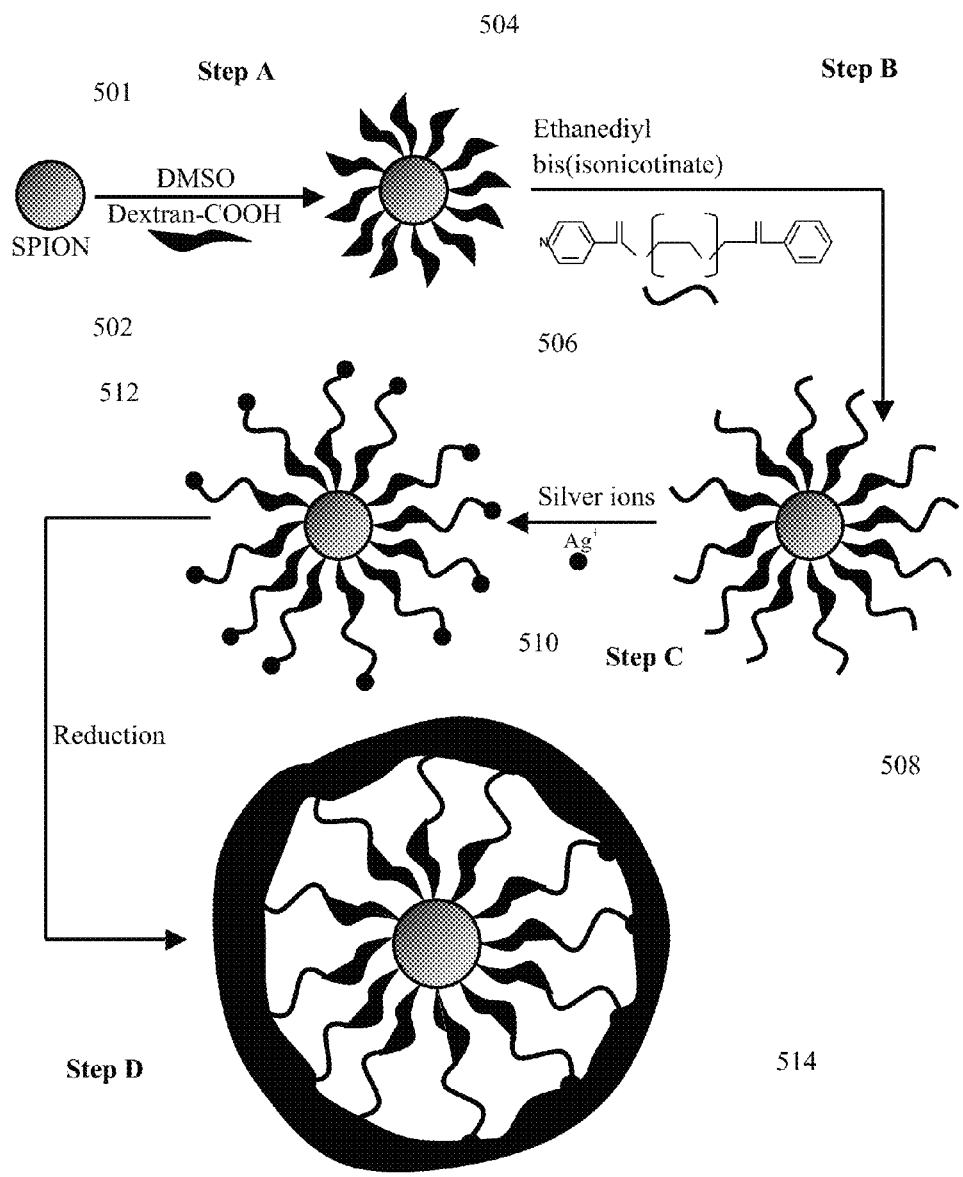
FIG. 5 shows a diagrammatic representation of the method of synthesizing the superparamagnetic iron oxide nanoparticle with a silver ring as a coating and a polymeric gap in between, according to an embodiment herein.

FIG. 5 shows a diagrammatic representation of the method of synthesizing the superparamagnetic iron oxide nanoparticle having a silver ring as a coating and a polymeric gap in between, according to an embodiment herein. With respect to FIG. 5, a monodisperse solution of superparamagnetic iron oxide nanoparticles SPION 501 is mixed with a solution of carboxylated dextran (Step A). The molecules of carboxylated dextran 502 spread over the surface of the spherical SPION 501 and form a layer by the ligand exchange phenomenon and further form an intermediate 504. The solution is further added with a solution of the ethanediyl bis(isonicotinate) compound (Step B). The molecules of ethanediyl bis(isonicotinate) compound 506 conjugate with the molecules of the carboxylated dextran 502 over the surface of the SPION 501 and further form an intermediate 508. The solution is added with a salt of silver ions (Step C). The molecules of ethanediyl bis(isonicotinate) compound 506 have a property of chelating with silver ions 510. The silver ions 510 conjugate over the molecules of the ethanediyl bis(isonicotinate) compound 506 to form an intermediate compound 512. This is followed by a step of reduction of the conjugated silver ions 510 over the surface of the intermediate 512 compound (Step D). The reduction of silver ions over the surface of the intermediate compound 512 leads to the formation of monodispersed silver ring-coated SPION 514 with a polymeric gap in between.

Figure 6:
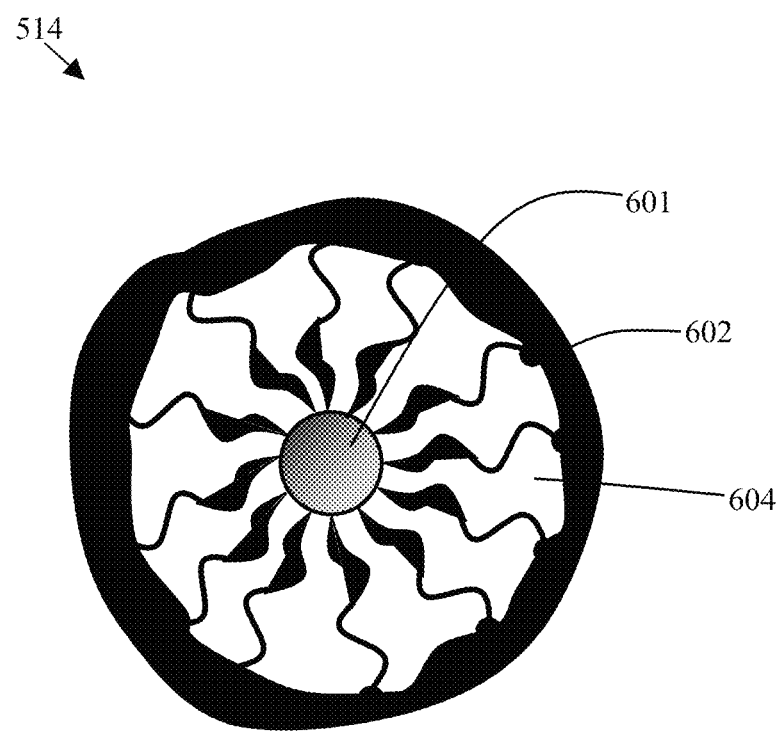
FIG. 6 shows a diagrammatic representation of the silver ring coated-SPION as synthesized in the FIG. 5, according to an embodiment herein.

FIG. 6 shows a diagrammatic representation of the silver ring coated-SPION 514 as synthesized in the FIG. 5, according to an embodiment herein. With respect to FIG. 6, the silver ring-coated SPION 514 has a core 601 made up of SPION 501 and an outer shell 602 made up of silver ions 510. In between the core 601 and shell 602 lies a gap 604. The gap 604 is a polymeric gap. The gap 604 is made up of the molecules of carboxylated dextran 502 and the molecules of the ethanediyl bis(isonicotinate) 506. The outer shell 602 looks like a ring. The SPION 514 has anti bacterial property. The SPION 514 stops the production of bacterial biofilms. The SPION 514 is completely compatible with the biological cells. The SPION 514 helps in the eradication of drug resistance caused by the bacteria to the drug.

Figure 7:
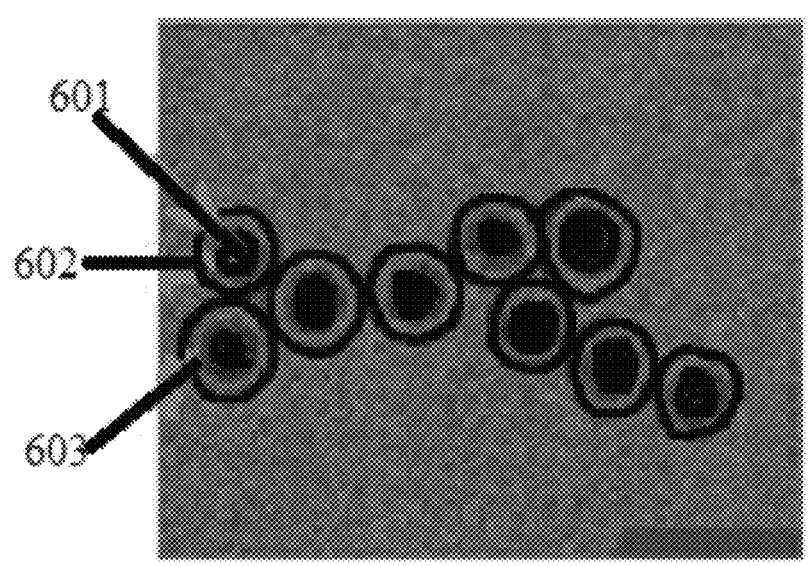
FIG. 7 shows a Transmission Electron Microscopy (TEM) image of the silver ring coated-SPION, according to an embodiment herein.

FIG. 7 shows a Transmission Electron Microscopy (TEM) image of the silver ring coated-SPION 514, according to an embodiment herein. With respect to FIG. 7, the SPION core 601 with an outer shell 602 and the gap 604 are clearly visible.

Figure 8:
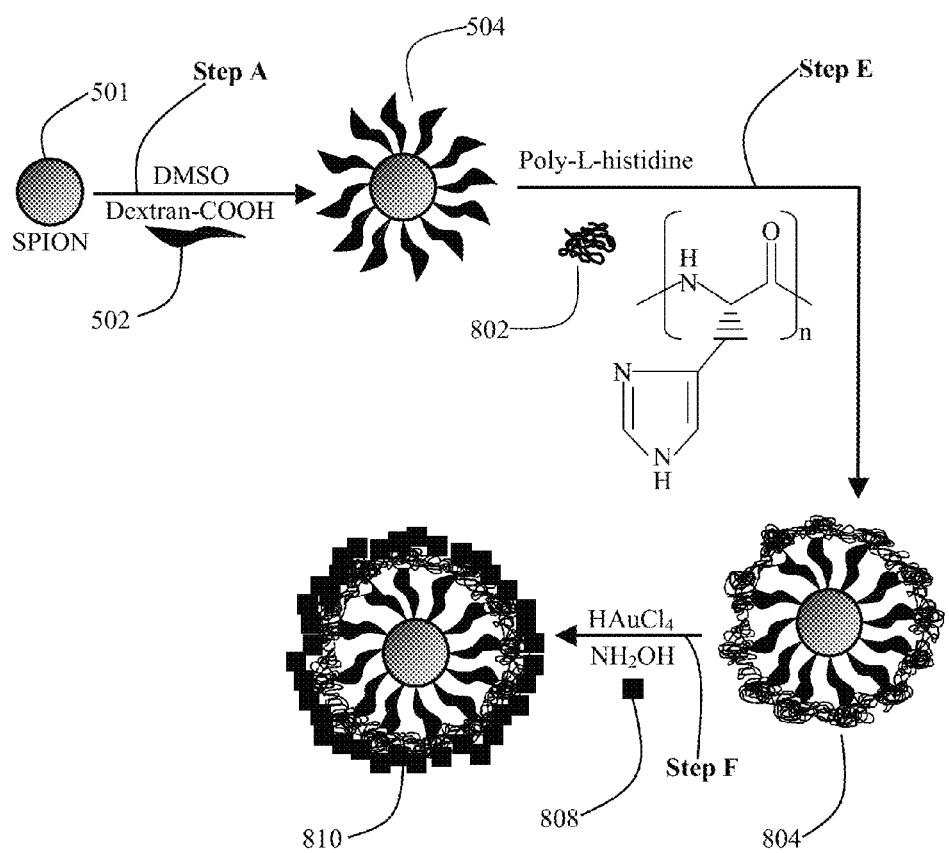
FIG. 8 shows a diagrammatic representation of the method of synthesizing the superparamagnetic iron oxide nanoparticle with a gold ring as a coating with a polymeric gap in between, according to prior arts.

FIG. 8 shows a diagrammatic representation of the method of synthesizing the superparamagnetic iron oxide nanoparticle having a gold ring as a coating with a polymeric gap in between, according to prior arts. With respect to FIG. 8, a monodisperse solution of superparamagnetic iron oxide nanoparticles 501 is mixed with a solution of carboxylated dextran (Step A). The molecules of carboxylated dextran 502 spread over the surface of the spherical SPION 501 and form a layer by the ligand exchange phenomenon and further form an intermediate compound 504. The solution is added with a solution of a polymer called poly-L-histidine (Step E). The molecules of poly-L-histidine 802 spread over the surface of the intermediate compound 504 and further forms an intermediate compound 804. The molecules of poly-L-histidine 802 get adsorbed on to the molecules of carboxylated dextran 502 by an electrostatic interaction. The solution is further added with a gold salt and a reducing agent (Step F). The gold salt is gold chloride ($HAuCl_4$) and the reducing agent is ammonium hydroxide. The molecules of poly-L-histidine 802 are capable of chelating gold ions 808. After the addition of the gold salt and the reducing agent, the gold ions 808 form a thin shell or a ring over the surface of the SPION 501 and finally give rise to a SPION 810 with a gold ring coating and a polymeric gap.

Figure 9:
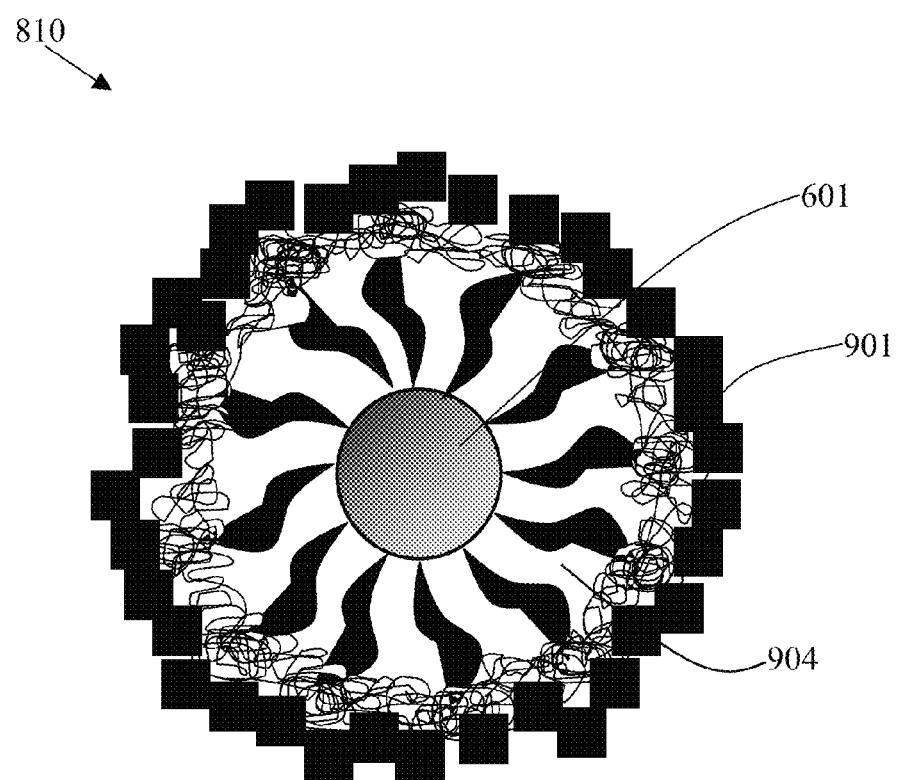
FIG. 9 shows a diagrammatic representation of the SPION with a gold ring coating and a polymeric gap synthesized in the FIG. 8, according to prior arts.

FIG. 9 shows a diagrammatic representation of the SPION 810 with a gold ring coating and a polymeric gap synthesized in the FIG. 8, according to prior arts. With respect to FIG. 9, the SPION 810 with a gold ring coating and a polymeric gap has a core 601. The core 601 is made up of SPION 501. An outer shell 901 made up of gold ions 808 surrounds the core 601. A polymeric gap 904 lies between the core 601 and the outer shell 901. The gap 904 is made up of the molecules of carboxylated dextran 502 and the molecules of the poly-L-histidine 802. The SPION 810 has anti bacterial property. The SPION 810 stops the production of bacterial biofilms. The SPION 810 is completely compatible with the biological cells. The SPION 810 helps in eradication of drug resistance caused by the bacteria to the drug.

Figure 10:
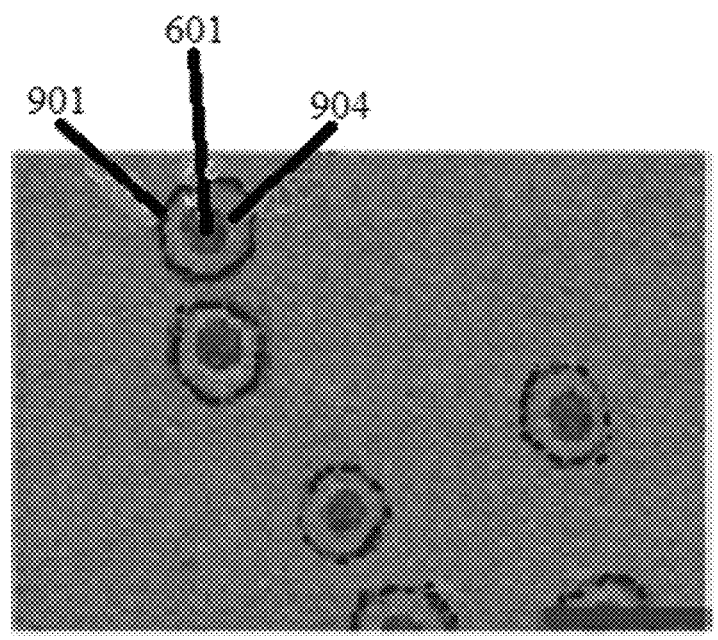
FIG. 10 shows a Transmission Electron Microscopy (TEM) image of the SPION with a gold ring coating and a polymeric gap, according to prior arts.

FIG. 10 shows a Transmission Electron Microscopy (TEM) image of the SPION 810 with a gold ring coating and a polymeric gap, according to prior arts. With respect to FIG. 10, the SPION 810 has a core 601 with an outer shell 901 and a polymeric gap 904. The core is made up of SPION 501. The outer shell is made up of gold ions 808 and the polymeric gap is made up of the molecules of carboxylated dextran 502 and the molecules of the poly-L-histidine 802.

Figure 11:
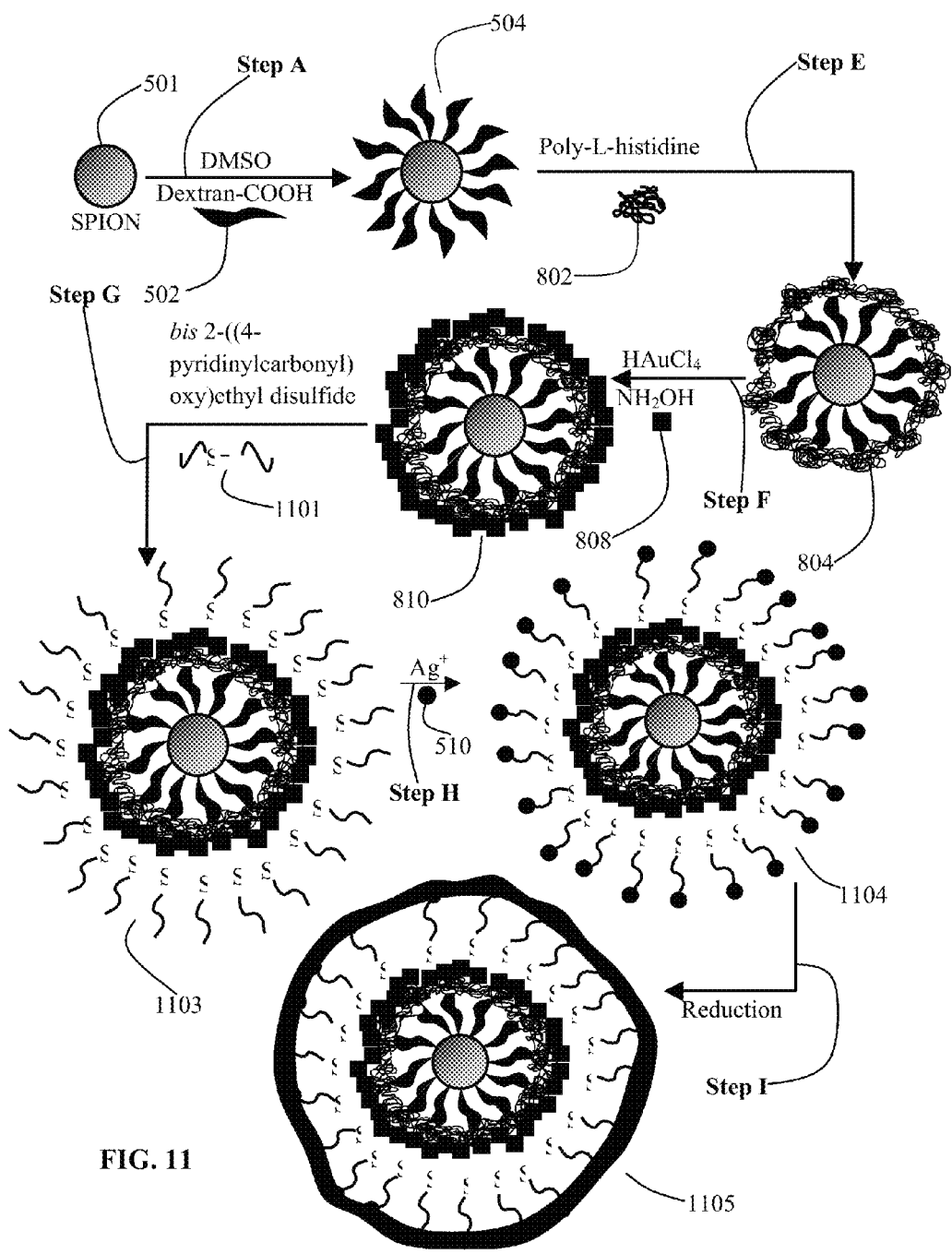
FIG. 11 shows a diagrammatic representation of the method of synthesis of both silver and gold coated SPIONS with a plurality of polymeric gaps, according to an embodiment herein.

FIG. 11 shows a diagrammatic representation of the method of synthesis of both the silver and gold coated SPIONS with a plurality of polymeric gaps, according to an embodiment herein. With respect to FIG. 11, the SPION 810 with a gold ring coating and a polymeric gap (formed by Step A, E and F in FIG. 8) further undergoes a surface treatment process. In the surface treatment process, the solution containing the gold coated SPIONs 810 are mixed with a solution containing a disulphide compound of bis 2-((4-pyridinylcarbonyl)oxy)ethyl disulfide (Step G). The molecules of compound bis 2-((4-pyridinylcarbonyl)oxy)ethyl disulfide 1101 form sulfide bonds over the surface of the gold coated SPIONS 810 and get accumulated to form the intermediate compound 1103. The solution is further added with a silver salt solution (Step H). The silver ions 510 binds on the molecules of bis 2-((4-pyridinylcarbonyl)oxy)ethyl sulfide compound 1101 on the surface of the SPION 810 to form an intermediate compound 1104. The solution is further reduced (Step I) by adding a reducing agent. The reducing agent is sodium borohydride. Finally, the SPIONs 1105 with gold and silver coatings having a plurality of polymeric gaps in between are formed.

Figure 12:
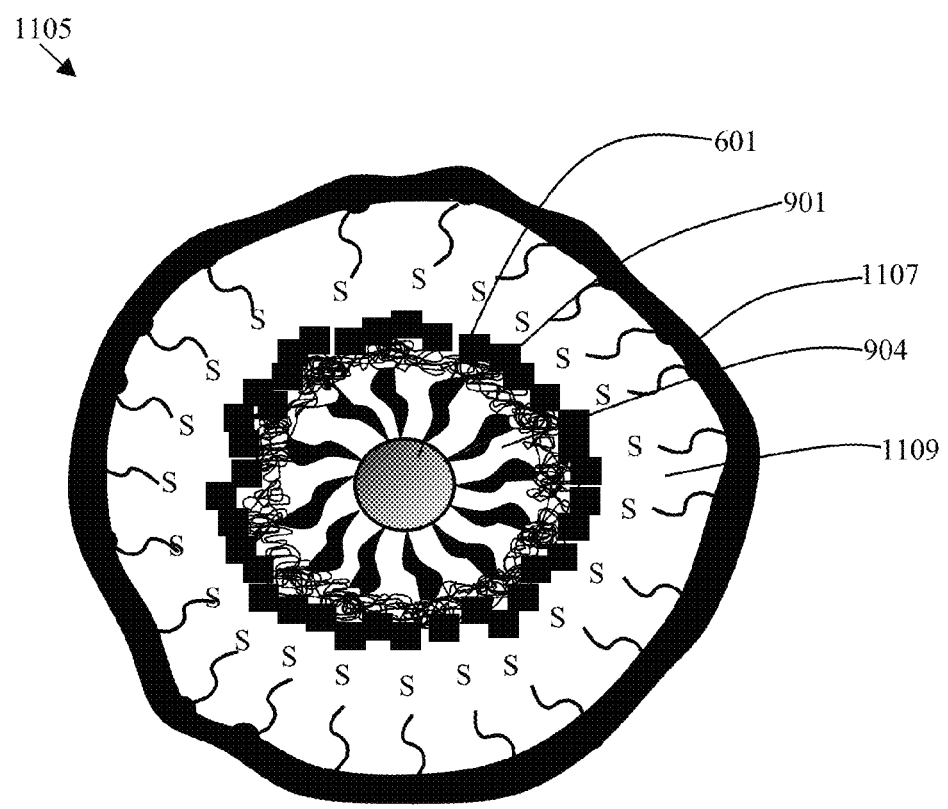
FIG. 12 shows a diagrammatic representation of the SPION with gold-silver coating and a plurality of polymeric gaps, according to an embodiment herein.

FIG. 12 shows a diagrammatic representation of the SPION 1105 with gold-silver coating having a plurality of polymeric gaps, according to an embodiment herein. With respect to FIG. 12, the core 601 of the SPION 1105 is surrounded by a gold shell 901. The gold shell 901 is further surrounded by a silver shell 1107. The two polymeric gaps 904 and 1109 lies in between the gold shell 901 and silver shell 1107. The polymeric gaps 904 and 1109 are made up of molecules of carboxylated dextran 502, molecules of ethanediyl bis(isonicotinate) compound 506, molecules of the poly-L-histidine 802 and molecules of bis 2-((4-pyridinylcarbonyl)oxy)ethyl disulfide compound 1101. Polymeric gap 904 is made up of molecules of carboxylated dextran 502, molecules of ethanediyl bis(isonicotinate) compound 506 and molecules of the poly-L-histidine 802. The molecules of carboxylated dextran 502, molecules of ethanediyl bis(isonicotinate) compound 506 and molecules of the poly-L-histidine 802 are arranged in a circumferential manner with molecules of carboxylated dextran 502 on inner side. The molecules of ethanediyl bis(isonicotinate) compound 506 are present on the outer region of the molecules of carboxylated dextran 502 followed by the molecules of the poly-L-histidine 802. Polymeric gap 904 is made up of molecules of bis 2-((4-pyridinylcarbonyl)oxy)ethyl disulfide compound 1101.

The Molecules of bis 2-((4-pyridinylcarbonyl)oxy)ethyl disulfide has a structural formula of (1):

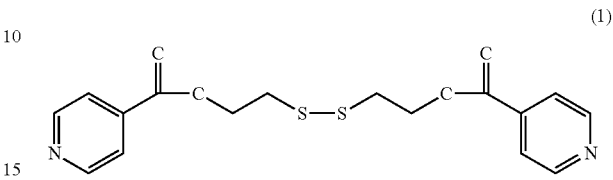

(1)

Figure 13:
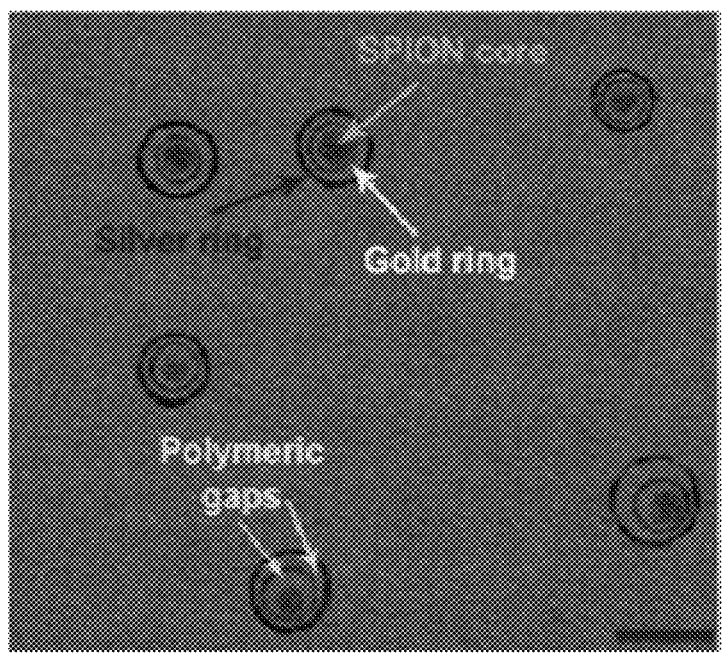
FIG. 13 shows a Transmission electron microscopy (TEM) image of the SPIONs with gold-silver rings or outer shells with a plurality of polymeric gaps, according to an embodiment herein.

FIG. 13 shows a Transmission electron microscopy (TEM) image of the SPIONs 1105 with gold-silver rings or outer shells with a plurality of polymeric gaps. With respect to FIG. 13, the SPION core with silver and gold rings having polymeric gaps in between is clearly visible.

According to an embodiment herein, the method of synthesis of silver ring coated SPIONs involves dispersing a monodispersed hydrophobic SPIONs in dimethyl sulfoxide (DMSO) in the presence of the carboxylated-dextran resulting in the assembly of hydrophilic coated SPIONs via a ligand exchange phenomenon. The Ethanediyl bis(isonicotinate) is then adsorbed into the outer surface of carboxylated-dextran coated particles through a charge-charge interaction. The distinguished characteristic of the ethanediyl bis(isonicotinate) polymer is its capability to absorb the silver ions on the outer surface of nanoparticles at a high packing density. The main function of multilayer organic molecules i.e. the carboxylate-dextran and the ethanediyl bis(isonicotinate)) deposited on the surface of SPIONs is to allow a direct growth of silver ions on the core of nanoparticles. These silver ions in turn give rise to the barrier or biofilm preventive characteristic of the coated SPIONs against the bacteria. Further a reduction of the highly-packed silver ions trapped at the surface of SPION by a reducing reagent leads to the formation of SPION-silver core-shell nanoparticles with clear polymeric gaps. The obtained particles are proposed to have suitable magnetic properties due to the existence of SPION as the core and antibacterial effects due to the presence of a thin layer of silver as the shell.

The function of the SPIONs according to the embodiments herein is further augmented to meet the properties required in diverse applications. For example, a surface enhanced Raman scattering (SERS)-based signal amplification and detection can be utilized to prepare the nanoparticles suitable for the molecular imaging and sensing applications. This study introduced a high-yield synthetic method for the preparation of SERS-active SPION-gold-silver, core-intermediate shell-shell multifunctional nanoparticles. The particles possess two polymeric gaps located between a core-intermediate shell and an intermediate shell-outer shell. The SERS active effect of gold-silver nano dumbbells was confirmed by atomic force microscope-correlated nano-Raman measurements of individual dumbbell structures. The results demonstrated that Raman signals can be repeatedly detected from the single-molecule-tethered nano dumbbells. Thus, the newly developed SPIONs provided in the embodiments herein can be employed as programmed smart reagents for single-DNA detection of pathogens which have promising impact on tackling the threats associated with the antibiotics resistance.

EXPERIMENTAL DATA

Materials: 90% of oleic acid and 1-octadecene were purchased from Sigma Aldrich (MO, USA). The Oleyl alcohol was purchased from TCI. The n-hexane was purchased from Samchun Chem (Seoul, Korea). The silver nitrate, sodium borohydride, kanamycin, isonicotinic acid, dextran having an average molecular weight of 5000, polyethylene glycol (PEG) having an average molecular weight of 400, poly(ethylene oxide) (6-arm, anthracene-terminated) having an average molecular weight of 12000, dimethylsulfoxide, sodium periodate, potassium cyanide, diethylene glycol, sodium hydroxide (NaOH), $NH_2OH.HCL$, gold salt ($HAuCl_4$) and Poly-L-histidine (PLH) were purchased from Sigma-Aldrich (Taufkirchen, Germany). PLH was used as template to direct gold nucleation and growth. Tryptone soy broth (TSB) was purchased from Oxoid ltd. (Basingstoke, United Kingdom).

Synthesis of Silver Nanoparticles: The silver nanoparticles were synthesized using a standard procedure. The procedure involves a reduction of silver nitrate. All of the experiments were done in a clean atmosphere to eliminate the chances of endotoxin contamination that may interfere with the toxicity profile of the nanoparticle. The silver nanoparticles were synthesized as control antibacterial particles in order to highlight the significance of the engineered nanoparticles. To prepare samples for TEM a drop of the suspension was placed on a copper grid and dried.

Figure 14:
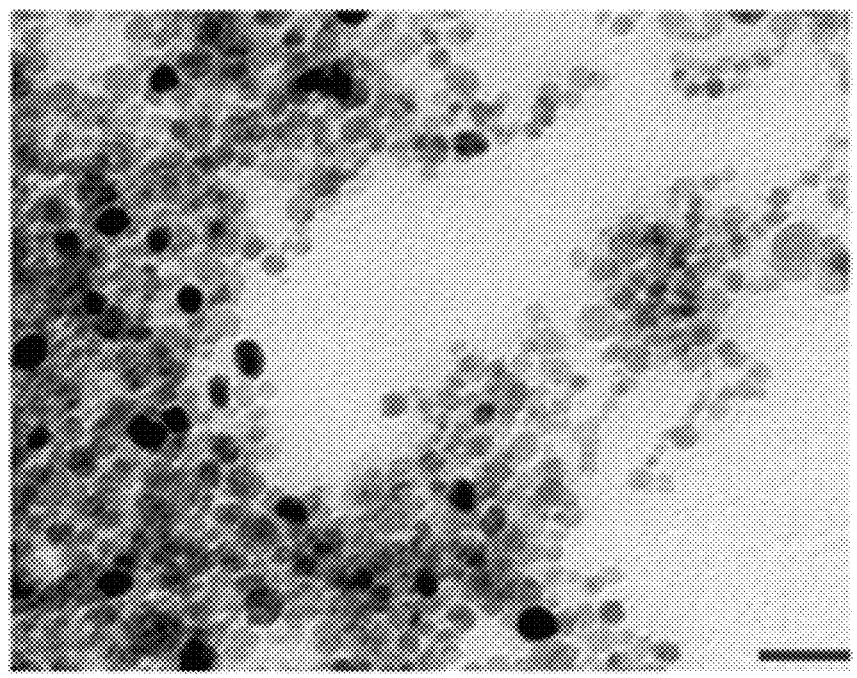
FIG. 14 shows a Transmission Electron Microscopy (TEM) image of silver nanoparticles, according to an embodiment herein.

FIG. 14 shows a Transmission Electron Microscopy (TEM) image of silver nanoparticles, according to an embodiment herein. With respect to FIG. 14, the synthesized silver nanoparticles are clearly visible. The nanoparticles are spherical in shape. The TEM image of FIG. 14 has a scale bar is 40 nm.

Figure 15:
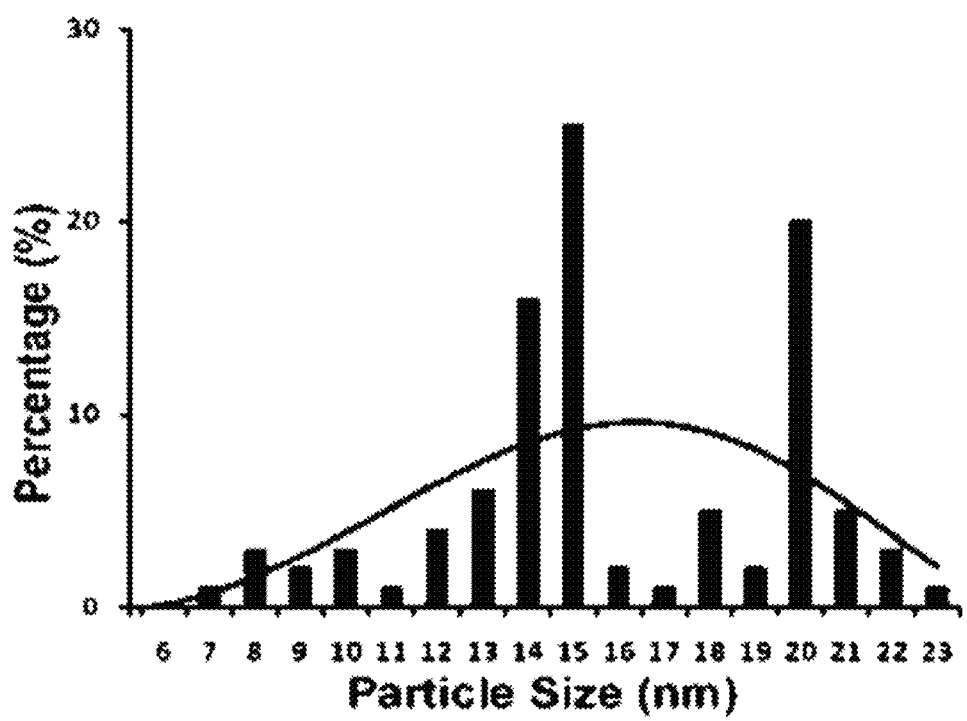
FIG. 15 represents a histogram indicating a size distribution of the synthesized silver nanoparticles, according to the embodiments herein.

FIG. 15 represents a histogram showing the size distribution of the synthesized silver nanoparticles, according to the embodiments herein. With respect to FIG. 15, the maximum particle size of the silver nanoparticles is between 10 nm-20 nm. The maximum percentage of silver nanoparticles is with a size of 15 nm.

Synthesis of Iron Oxide Nanoparticles: The SPIONs were synthesized according to a previously reported procedure. Briefly, the iron-oleate complexes were prepared by reacting sodium oleate and iron (III) chloride. The SPIONS were synthesized with an average size of 13 nm. For the synthesis of SPIONs with an average size of 13 nm, 18 g of iron-oleate complex with 20 mmol concentration and 5.7 g of oleic acid with 20 mmol concentration were dissolved in 100 g of 1-octadecene at room temperature. The reaction mixture was degassed at 80° C. for 2 hrs. The mixture was heated to a reflux temperature at a heating rate of 3° C./minute and then kept for 30 minutes under an inert atmosphere. The container vessel was rapidly cooled down to the room temperature after the reaction occurred. This was followed by the addition of 500 mL of acetone to start the precipitation of SPIONs. The SPIONs were separated by a centrifuge and dispersed in hexane.

Figure 16:
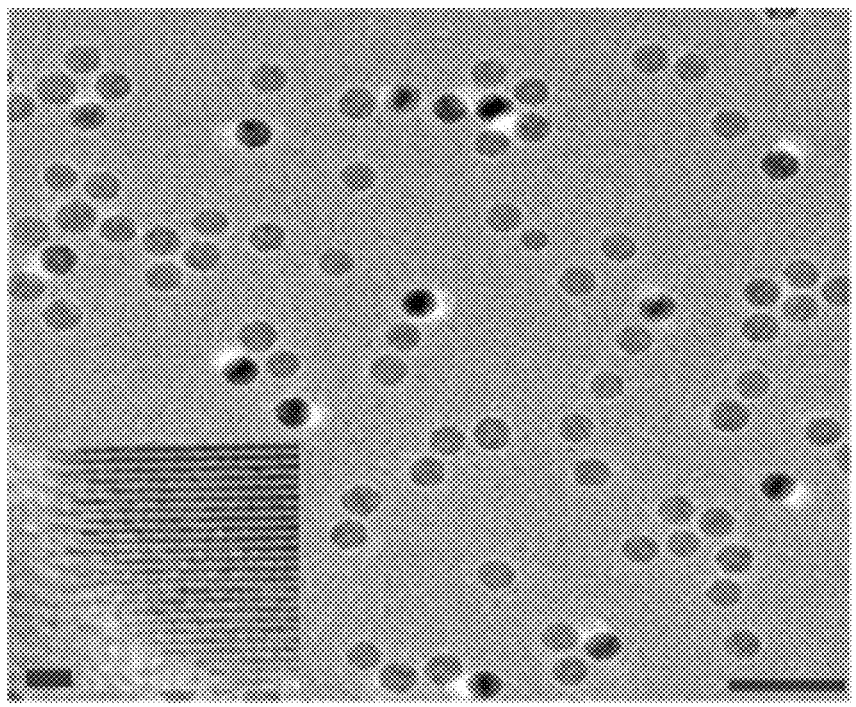
FIG. 16 shows a Transmission Electron Microscopy (TEM) image of bare superparamagnetic iron oxide nanoparticles (SPIONs), according to the embodiments herein.

FIG. 16 shows a Transmission Electron Microscopy (TEM) image of bare superparamagnetic iron oxide nanoparticles (SPIONs), according to the embodiments herein. With respect to FIG. 16, the synthesized superparamagnetic iron oxide nanoparticles are clearly visible. The scale of the TEM image of FIG. 16 is 40 nm.

Preparation of the Carboxyl-Dextran:

The Carboxylated-dextran was prepared according to the procedure reported elsewhere. The hydroxyl groups in dextran were oxidized to aldehydic groups at first using sodium periodate. Briefly, the sodium periodate was dissolved in de-oxygenated DI water and introduced to dextran solution. The dextran used had a molecular weight of 5000. The dextran solution was prepared by dissolving 4 g of dextran in 30 mL of de-oxygenated DI water. The solution was homogenized for 2 hrs at room temperature followed by dialyzing with a membrane bag (1,000 cut-off molecular weight) for 4 days. Cyanohydrins intermediate was prepared via an interaction between the obtained solution and potassium cyanide. Finally, the carboxylic acid groups were created at the terminal units of dextran through the hydrolysis of the obtained cyanohydrins intermediate. The prepared carboxylated dextran was lyophilized and stored at −80° C.

Carboxyl-Dextran Coated SPIONs: In order to coat the prepared hydropobic SPIONs with carboxylated-dextran the ligand exchange process was employed. In this case, SPIONs with an iron concentration of 1 mg/ml were produced and mixed with the dextran ligands placed in DMSO dipolar solvent. The reactions between the nanoparticles and polymer were conducted at a room temperature for 72 hrs while shaking in the incubator. DMSO can make homogeneous solutions with both aqueous polymer substrates and organic solvents. Then, 1 mL of stock SPION solution was mixed with carboxylated-dextran in 30 mL of DMSO. The coated SPIONs were magnetically collected through a strong magnetic field using a magnetic-activated cell sorting (MACS®) system once the reaction was complete and redispersed into 1 mL of DI water. These water-soluble SPIONs were completely stable at room temperature without a detectable precipitation.

Synthesis of the Smooth Silver Ring-Coated SPIONs with Polymeric Gap: In order to deposit a silver ring-shell on the surface of carboxylated-coated SPIONs with a polymeric gap, the ethanediyl bis(isonicotinate) was utilized to interact with the silver ions. The ethanediyl bis(isonicotinate) was derived from the biocompatible components isonicotinic acid and polyethylene glycol (PEG) units and was added to the carboxylated-coated SPIONs (0.5 μM) for 20 minutes. The obtained particles were rinsed for several times with DI water and collected by MACS system. The accumulated particles were redispersed in the DI water containing 1 μM silver nitride and mixed for additional 20 minutes. Subsequently, the particles were separated again by MACS. For the preparation of the silver ring-shell, the silver ions which were linked to ethanediyl bis(isonicotinate) coated SPIONs were reduced by a redispersion of the particles in DI water containing sodium borohydride. The obtained silver ring coated SPIONs with a polymeric gap were fixed in MACS systems and washed by DI water. After redispersion in DI water the produced particles were stored at 2-8° C.

Figure 17:
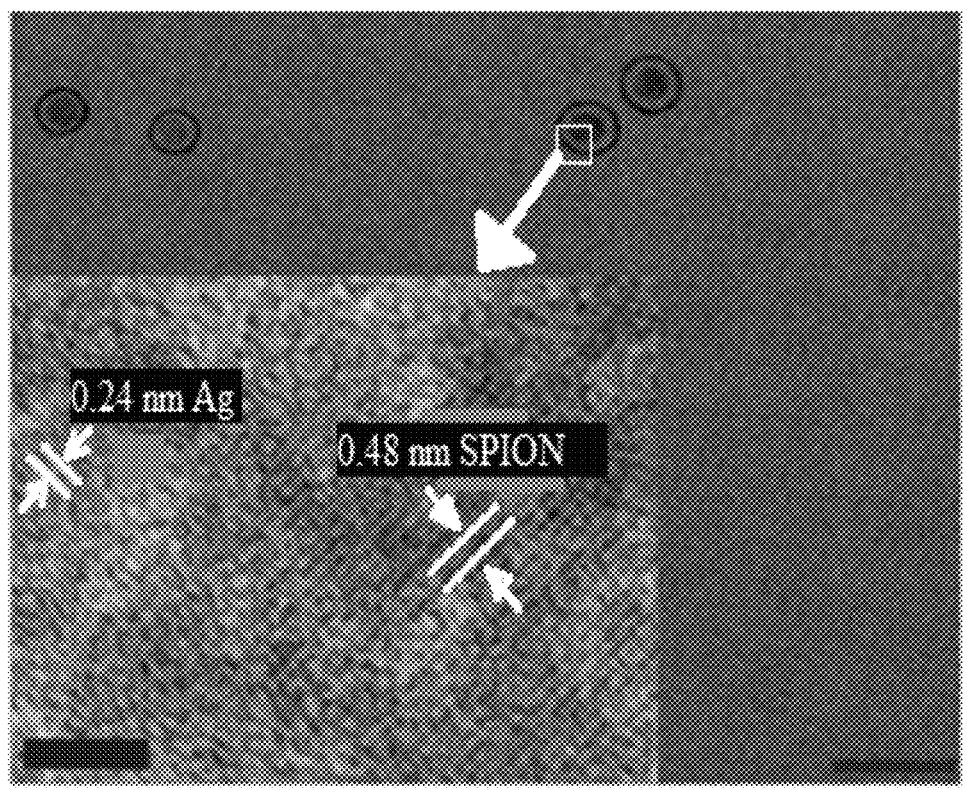
FIG. 17 shows a Transmission Electron Microscopy (TEM) image of silver coated superparamagnetic iron oxide nanoparticles (SPIONs) with polymeric gap, according to an embodiment herein.

FIG. 17 shows a Transmission Electron Microscopy (TEM) image of silver coated superparamagnetic iron oxide nanoparticles (SPIONs) with polymeric gap, according to an embodiment herein. With respect to FIG. 17, the silver coated superparamagnetic iron oxide nanoparticles (SPIONs) with polymeric gap are visible. The TEM scale bar is 40 nm. The polymeric gaps are not properly visible under the TEM image because of their low electron densities. The panel in the left side corner of the FIG. 17 shows a high resolution TEM image of the silver coated SPIONs. The scale bar for the panel is 1 nm. The lattice spacing of the silver shell is 0.24 nm for (111) crystal planes of face-centred cubic (fcc) silver. The lattice spacing of the SPION is 0.48 nm corresponding to its (111) plane.

Synthesis of the Smooth Gold Ring-Coated SPIONs with Polymeric Gap: The smooth gold-shell SPIONs were produced according to a previous report. Briefly, the carboxylated-dextran coated SPIONs were immersed in Poly-L-Histidine (PLH) at the pH of 5-6. The pH adjustment was done using 0.1 N HCl. After incubation for 60 minutes the coated SPIONs were collected using a magnet and rinsed several times by DI water. The obtained solution was mixed with 1% w/w solution $HAuCl_4$ for 20 minutes with the pH adjusted at 9-10 using NaOH. Subsequently, $NH_2OH.HCL$ was added to the solution and mixed well until the color of the colloidal suspension turned dark blue. The color change was visible within few minutes. The solution was then washed several times, redispersed in DI water using a sonicator and stored at 2-8° C. for silver coating process.

Figure 18:
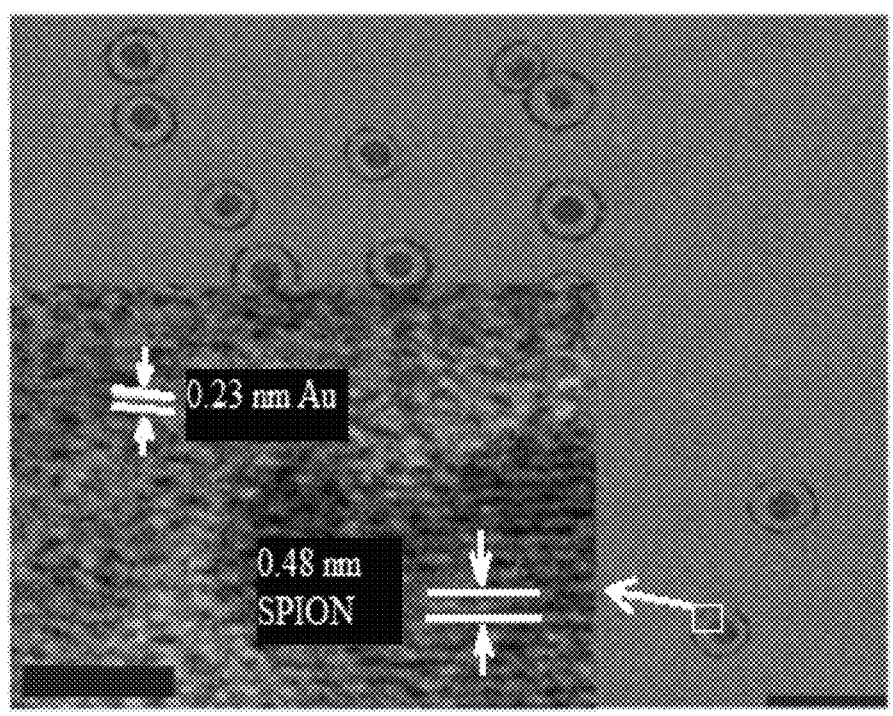
FIG. 18 shows a Transmission Electron Microscopy (TEM) image of gold coated superparamagnetic iron oxide nanoparticles (SPIONs) with polymeric gap, according to an embodiment herein.

FIG. 18 shows a Transmission Electron Microscopy (TEM) image of gold coated superparamagnetic iron oxide nanoparticles (SPIONs) with polymeric gap, according to an embodiment herein. With respect to FIG. 18, the gold coated superparamagnetic iron oxide nanoparticles (SPIONs) with polymeric gap are visible. The TEM scale bar is 40 nm. The polymeric gaps are not properly visible under the TEM image because of their low electron densities. The panel in the left side corner of the FIG. 18 shows a high resolution TEM image of the gold coated SPIONs. The scale bar for the panel is 1 nm. The lattice spacing of the silver shell is 0.23 nm for (111) crystal planes of face-centred cubic (fcc) gold. The lattice spacing of the SPION is (148 nm corresponding to its (111) plane.

Synthesis of the Smooth Silver-Coated Gold Ring-Coated SPIONs with Double Polymeric Gaps:

The gold-ring coated SPIONs with polymeric gap were collected by MACS systems and redispersed in 5 ml of disulfide solution. The disulfide solution was 5 mM of bis 2-((4-pyridinylcarbonyl)oxy)ethyl disulfide dissolved in 100 ml $CH_2Cl_2$-EtOH in 1:1 ratio. The solution was mixed well for 5 hours. The gold coated particles were fixed in MACS, rinsed with EtOH and immediately redispersed in 0.5 μM of ethanediyl bis(isonicotinate) solution. After a homogenization for 20 minutes, the particles were collected by MACS and redispersed in DI water solution containing silver nitride. This was followed by homogenization for additional 20 minutes. Processed particles were collected by MACS and washed several times by DI water and reduced by a redispersion of the particles in DI water containing sodium borohydride. The obtained silver ring-shell coated gold intermediate-shell SPIONs with double polymeric gap were fixed in MACS and washed by DI water followed by a redispersion in DI water and storage at 2-8° C. for future work.

Figure 19:
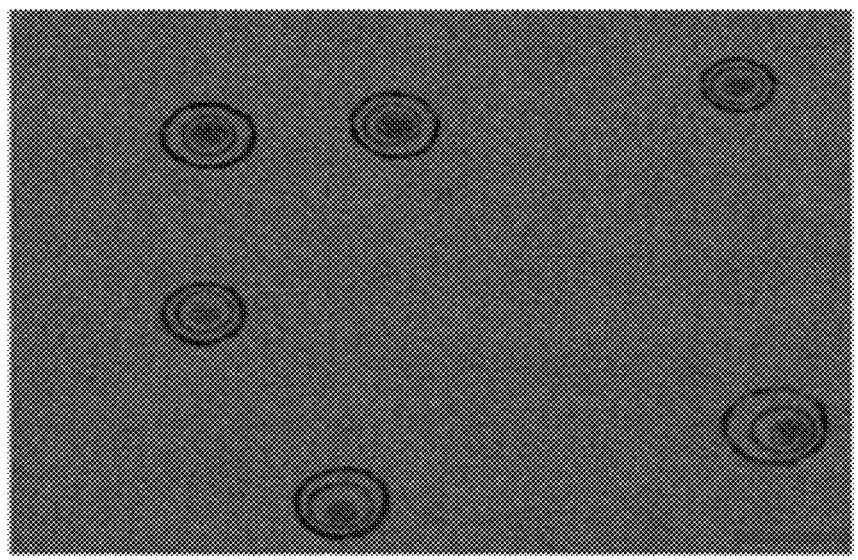
FIG. 19 shows a Transmission Electron Microscopy (TEM) image of silver and gold coated superparamagnetic iron oxide nanoparticles (SPIONs) with polymeric gaps, according to an embodiment herein.

FIG. 19 shows a Transmission Electron Microscopy (TEM) image of silver and gold coated superparamagnetic iron oxide nanoparticles (SPIONs) with polymeric gaps, according to an embodiment herein. With respect to FIG. 19, the SPIONs with two rings and two gaps are visible. The two rings are gold and silver ring, respectively. The gaps are polymeric gaps according to the embodiments herein.

The Transmission electron Microscopic (TEM) micrographs revealed that all of the prepared multifunctional particles were mono dispersed and the shell thickness of both gold and silver rings was approximately 2-3 nm. The particles also exhibited a transparent gap with a size of ~3-5 nm between the core and shell and also between the intermediate and outer shells. The appearance of these features was due to the fact that sandwiched organic materials are not electron-dense enough for TEM visualization. The formed polymeric gaps confirmed that gold and silver shells were not deposited directly on the surface of the core but were template-coated via the polymeric outer layer.

Characterization of the Spions Synthesized to the Embodiments Herein

The size and shape of the produced nanoparticles were evaluated by using a Phillips CM200 transmission electron microscope (TEM; Eindhoven, the Netherlands). Live/Dead and MTT assays were performed in 10 separate experiments with the results expressed as mean±standard deviation. The standard deviation values are indicated as error bars in the results plots. The results were statistically processed for outlier detection using a "Tprocedure" using MINITAB software (Minitab Inc., State College, Pa.). One-way analysis of variance (ANOVA) with $p<0.05$ was performed for each set of test repeats. Outlier samples were excluded from the corresponding assays viabilities calculations.

Figure 20:
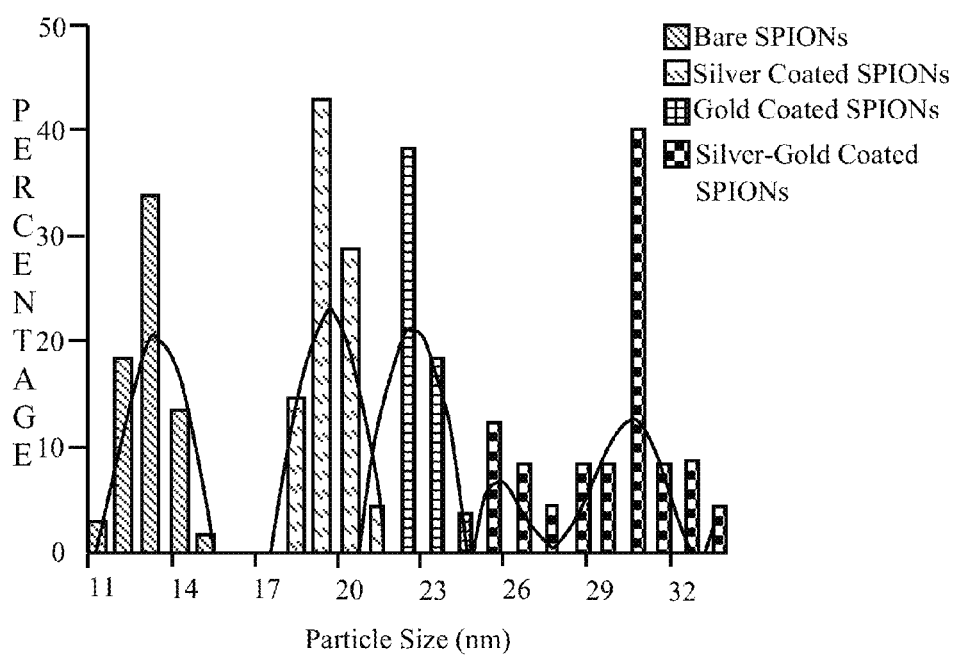
FIG. 20 shows the histograms indicating a size distribution for the bare SPIONs, silver coated SPIONs, gold coated SPIONs and silver-gold coated SPIONs according to the embodiments herein.

FIG. 20 shows histograms indicating the size distribution for the bare SPIONs, silver coated SPIONs, gold coated SPIONs and silver-gold coated SPIONs that were synthesized according to the embodiments herein. The particle size histograms are plotted from analysis of more than 50 particles for each sample. With respect FIG. 20, the particle size of the SPIONs increased with the increase in number of rings.

Figure 21:
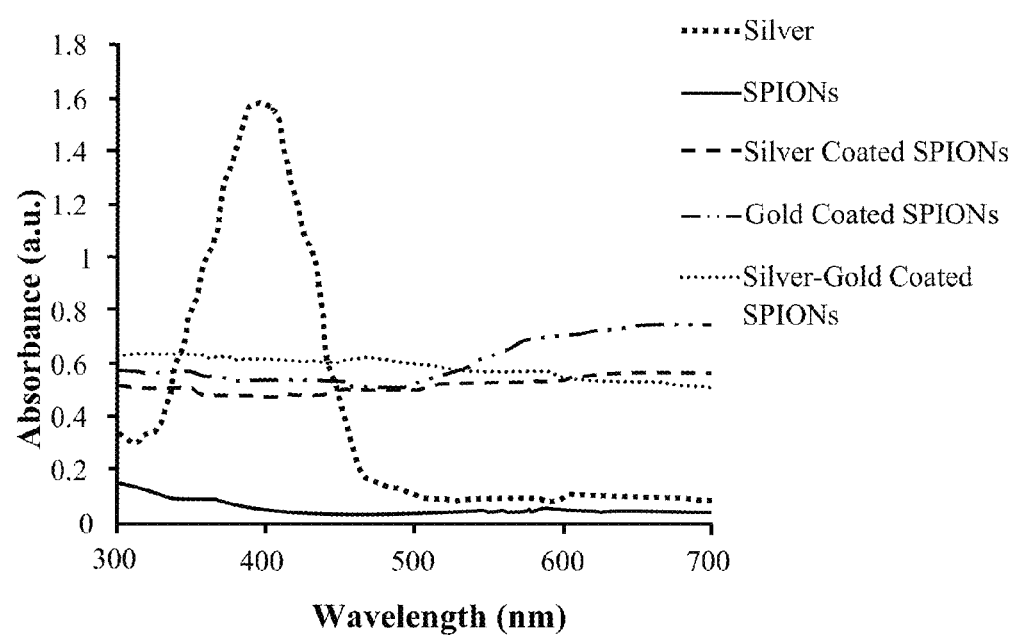
FIG. 21 shows the extinction spectra of the silver, bare SPIONs, silver coated SPIONs, gold coated SPIONs and silver-gold coated SPIONs, according to the embodiments herein.

FIG. 21 shows an extinction spectra of the bare SPIONs, silver coated SPIONs, gold coated SPIONs and silver-gold coated SPIONs that were synthesized according to the embodiments herein. It is well known that gold and silver nanoparticles show significant absorbance peaks due to their surface plasmon resonance (SPR) capability. However, it has been reported that by creating gold nanoshells, the SPR band of gold nanoparticles is transferred to near infrared (NIR) spectrum based upon the thickness of the shells. With respect to FIG. 21, the Surface Plasmon Resonance (SPR) peaks of both gold and silver coated SPION were widened and transferred to the Near Infrared region. The observed peak broadening is attributed to the several factors that emerge in the core shell particles for example phase-retardation effects, size distribution of both cores and shells and electron scattering at shell interfaces. In contrast, the SPR peaks did not shift to lower wavelengths even in the case of gold coated SPIONs and silver coated SPIONs. This may be related to the fluorescence quenching effect which has been also in gold coated quantum dots.

The magnetization measurements were performed on solid samples i.e. dry powder using a Quantum Design Superconducting Quantum Interference Device MPMS-XL7 magnetometer. Hysteresis experiments in the range of $-5T \le H \le +5T$ were conducted at T=300K. In order to characterize the absorption spectra of nanoparticles, UV/vis spectroscopy of the samples was performed using a Lambda 950 spectrophotometer (PerkinElmer, USA) from 300 to 700 nm wavelengths. The magnetic properties of nanoparticles were evaluated using the Quantum Design Superconducting Quantum Interference Device (SQUID). The dual toxicology effect of multifunctional nanoparticles in bacteria and human cells was analyzed. The magnetization verses the magnetic field at 2K and 300K for all nanoparticles exhibit the suitable magnetic properties of antibacterial particles for penetration in biofilms was analyzed.

Figure 22:
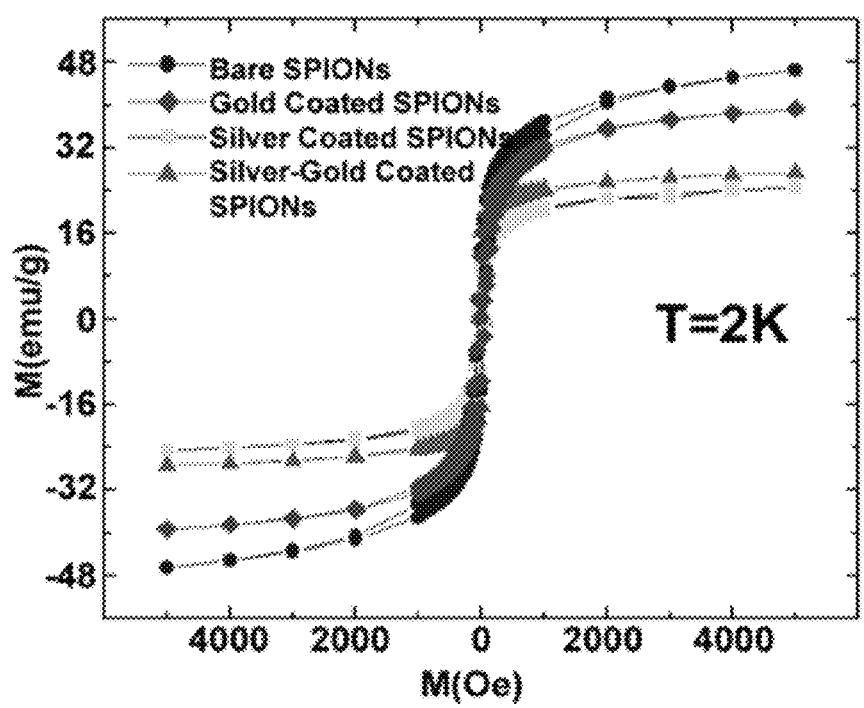
FIG. 22 shows a hysteresis curve for the bare SPIONs, silver coated SPIONs, gold coated SPIONs and the silver-gold coated SPIONs collected at Temperature=2K, according to the embodiments herein.
Figure 23:
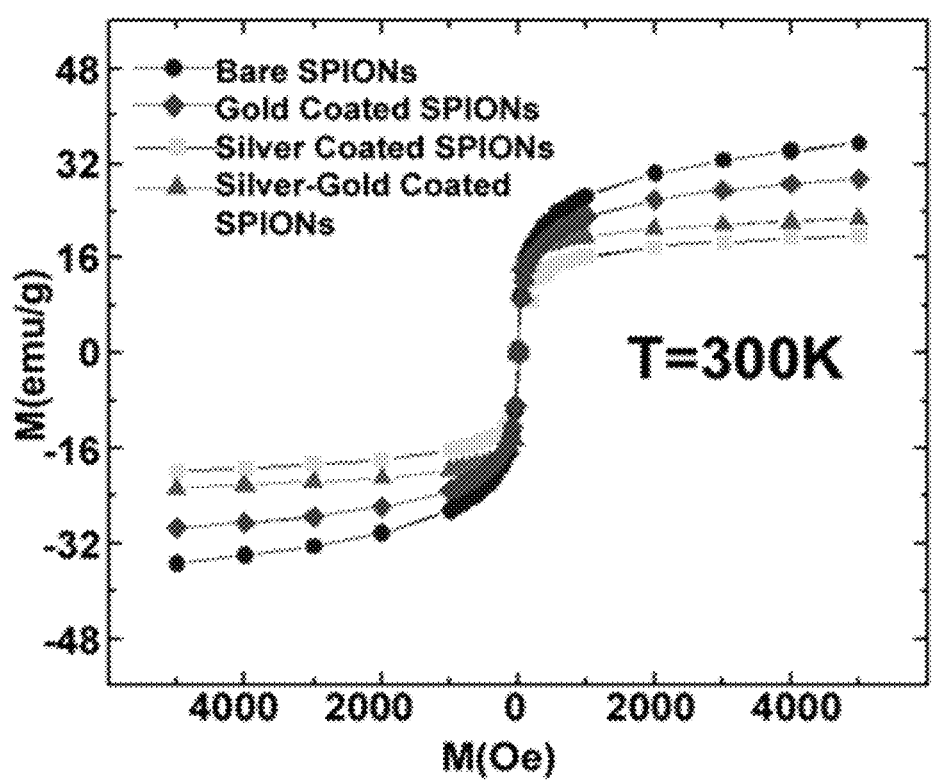
FIG. 23 shows a hysteresis curve for the bare SPIONs, silver coated SPIONs, gold coated SPIONs and silver-gold coated SPIONs collected at Temperature=300K, according to the embodiments herein.

FIG. 22 shows a hysteresis curve for the bare SPIONs, silver coated SPIONs, gold coated SPIONs and the silver-gold coated SPIONs collected at Temperature=2K, according to the embodiments herein while FIG. 23 shows a hysteresis curve for the bare SPIONs, silver coated SPIONs, gold coated SPIONs and silver-gold coated SPIONs collected at Temperature=300K, according to the embodiments herein. With respect to FIG. 22, the hysteresis was slightly open with small coercive fields at low temperature i.e. 2K while with respect to FIG. 23 there was no hysteresis loop seen at 300K. This indicates the super paramagnetic properties of the nanoparticles. All of the multifunctional particles demonstrated magnetic saturation amounts that are adequate for particles penetration within the bacterial biofilms. Due to their higher shell thickness, the saturation magnetization of SPION-gold silver nanoparticles was slightly lower than that in the SPION-silver particles.

Growth of Adhering Bacteria in Absence and Presence of Various Nanoparticles:

*Staphylococcus aureus* (ATCC 19636) and *Staphylococcus epidermidis* (ATCC 35984) were employed for the evaluation of the antibacterial effects of various particles. *Staphylococci* were first grown aerobically overnight at 37° C. on blood agar from a frozen stock. The plate was kept at 4° C. For each experiment, one colony was inoculated in 10 mL of Tryptone Soy Broth (TS) and cultured for 16 hrs. Bacteria were harvested by centrifugation at 5000×g for 5 minutes at 10° C. and washed with sterile Phosphate Buffer Solution. Then, the washed bacteria were suspended in Tryptone Soy Broth (TSB) to a concentration of $10^5$ bacteria/mL.

Further the 100 μL of bacterial suspension was put in each well of polystyrene 96-well plates (NUNC MaxiSorp, Nunc A/S, Roskilde, Denmark) in the absence or presence of various nanoparticles. The total metal ions with a concentration of 80 μg/ml were used. This concentration contains silver (Ag) ions for silver nanoparticles or the sum of silver (Ag), gold (Au) and iron (Fe) ions concentrations for silver-ring gold-shell SPIONs. Bacteria were allowed to grow aerobically at 37° C. for 24 hrs. In addition to the role of particles, the effect of the presence of an antibiotic was also examined. For this purpose, 1 μg of an aminoglycoside antibiotic called kanamycin was added. Kanamycin is generally used for the treatment of a wide variety of infections. Experiments with kanamycin (antibacterial drug) were carried out on bacteria for confirmation of strong antibacterial effects of multifunctional particles. The Percentage of dead bacteria in 24 h old staphylococcal biofilms of *S. aureus* and *S. epidermidis* with and without external magnetic field in absence and presence of various particles were calculated.

Subsequently, the wells were rinsed with Phosphate Buffer Solution and unbound bacteria were removed. In order to assess the viability of adhering staphylococci after 24 hrs of the biofilm growth, LIVE/DEAD® BacLigh™ Bacterial Viability Kit (Molecular Probes Inc., Oregon, USA) was employed. The kit consists of two probes: SYTO9 is a membrane-permeant nucleic acid stain (green fluorescence at 530 nm upon excitation at 488 nm) that labels the living bacteria. The second probe is propidium iodide (PI, red fluorescence at 620 nm upon excitation at 488 nm) that enters only the bacteria with compromised membranes. After staining with the kit, the plates were incubated for 15 minutes in the dark at the room temperature. The fluorescence intensities were measured by using a 96-well fluorescence microplate reader (CA, USA). Measurements were performed 10 times on separately cultured bacteria.

Penetration of Magnetic Particles During Biofilm Growth: Each well of 96-well plates was filled with 100 μL of either *Staphylococcus aureus* or *Staphylococcus epidermidis* suspensions. The bacteria were allowed to adhere and grow aerobically at 37° C. for 24 hrs in the absence or presence of various nanoparticles. An external magnetic field was applied by placing the plates on top of a strong permanent magnet. Subsequently, wells were rinsed with Phosphate Buffer Solution and unbound bacteria were removed. The bacteria viability was assessed using the LIVE/DEAD® assay as described in the previous section. Experiments were repeated 10 times using separately cultured bacteria.

Figure 24:
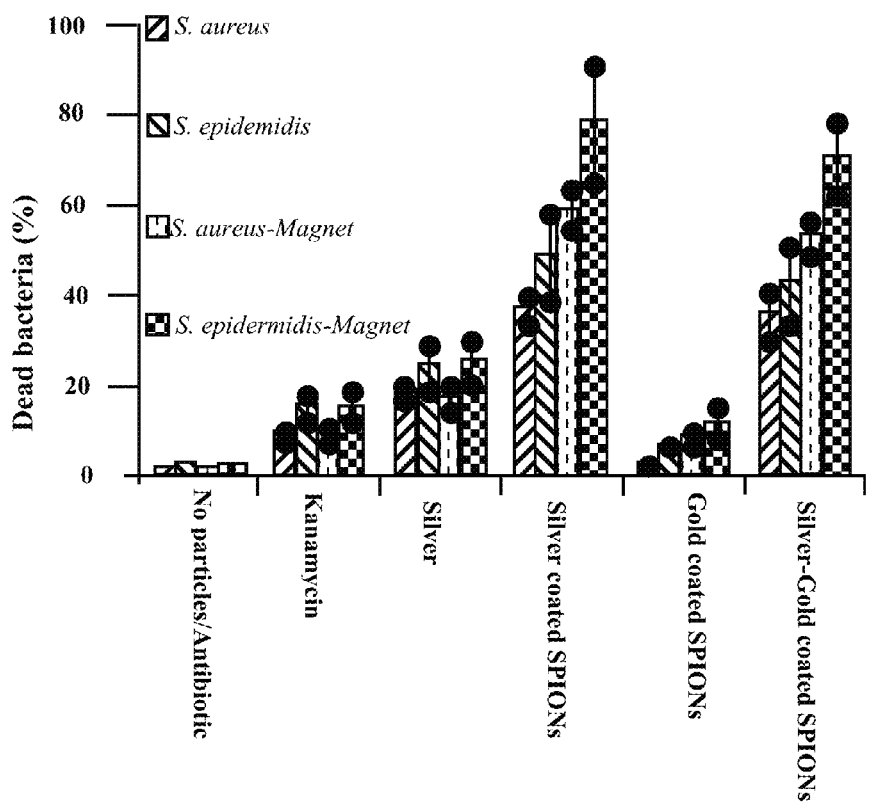
FIG. 24 shows a graphical representation indicating the percentage of dead bacteria in presence of an antibacterial drug such as silver nanoparticles, silver coated SPIONs, gold coated SPIONs and silver-gold coated SPIONs, according to the embodiments herein.

FIG. 24 shows a graphical representation illustrating the percentage of dead bacteria in presence of antibacterial drug, silver nanoparticles, silver coated SPIONs, gold coated SPIONs and silver-gold coated SPIONs, according to the embodiments herein. With respect to FIG. 24, the error bars represents standard deviation over ten independent experiments. As concluded from FIG. 24, it was seen that when exact same particle concentration was used the percentage of dead bacteria in the biofilms was significantly higher in the presence of either silver coated SPIONs or silver-gold coated SPIONs than that in the presence of silver nanoparticles. Interestingly, the gold coated SPIONs exhibited no differences in the percentage of dead bacteria when compared to that in the control for both bacteria types. The effect of the external magnetic field of both silver-coated SPIONs (i.e. SPION-silver and SPION-gold-silver nanoparticles) on the *Staphylococcus epidermidis* and *Staphylococcus aureus* biofilms was a significant increase in the amount of the dead bacteria. However, no difference was detected between non-magnetic particles and drug treated bacteria. There was a slight increase in the amount of dead bacteria for gold coated SPIONs. This can be attributed to the penetration of the nanoparticles within the biofilm and increasing their total amount in the bacteria layer.

In Vitro Biocompatibility Assessment:

In order to assess the toxicity effects of the manufactured nanoparticles on the cells a human liver carcinoma cell line was utilized. The human liver carcinoma cell line was HepG2. This cell line was treated with various nanoparticles at different concentrations.

Human liver carcinoma cell line ($HepG_2$ (ATCC HB-8065)) were seeded on 96-well plates at 10,000 cells per well in 150 μL of medium and incubated for 24 hrs. The cells were cultured in Dulbecco's modified Eagle's medium (DMEM) supplemented with 10% fetal bovine serum (FBS) at 37° C. in a 5% $CO_2$ incubator. After the 24-hour incubation period, 40 μL of medium containing various nanoparticles with a total metal ions concentration of 80 μg/ml was added to each well and cells were incubated for additional 24 hrs. The control cells were incubated with the same culture medium without the nanoparticles. Different particle concentrations and controls were each seeded in 10 separate wells. Cytotoxicity of the nanoparticles was assessed using the modified MTT (3-(4,5-dimethylthiazol-2-yl)-2,5-diphenyltetrazolium bromide) assay. After 24 hrs of incubation of the cell with or without the nanoparticles, 100 μL of MTT of 0.5 mg/mL concentration was added to each well. Following 3 hr incubation, the medium was removed and formazan crystals were solubilized by incubation in 150 μL of isopropyl alcohol for 20 minutes. The absorbance of each well as an indicator of the cells viability was read at 545 nm using a microplate reader (Stat Fax-2100, Awareness, Palm City, Fla.).

Figure 25:
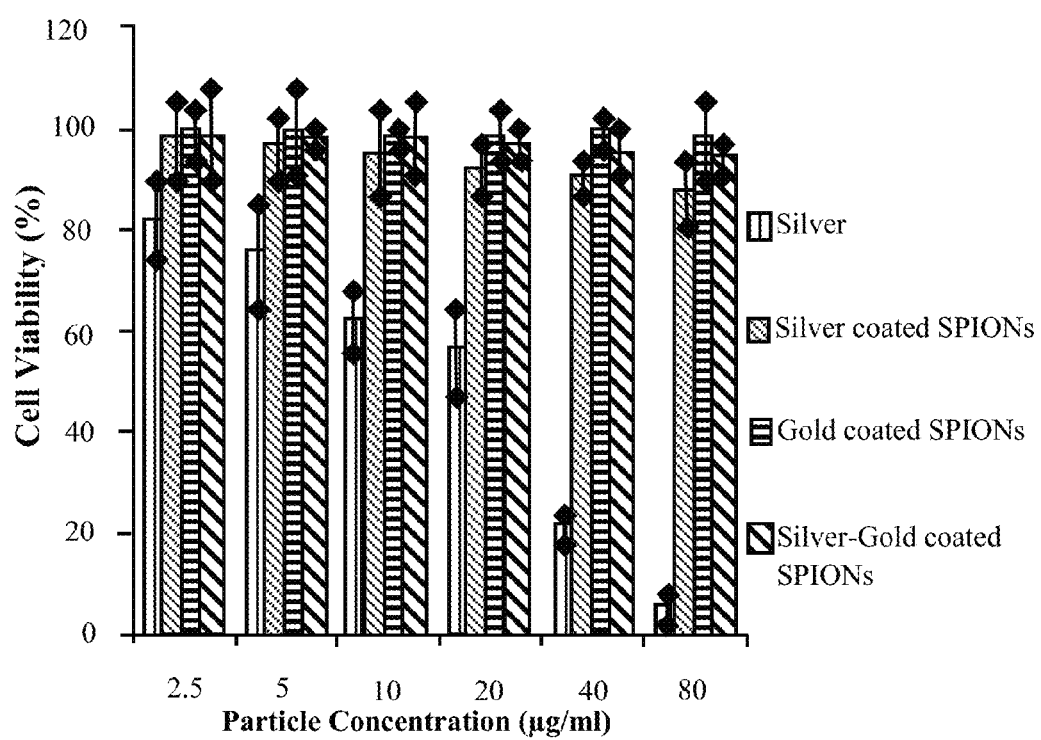
FIG. 25 shows a graphical representation indicating the effects of viability on the human liver carcinoma cell line in the presence of silver nanoparticles, silver coated SPIONs, gold coated SPIONs and silver-gold coated SPIONs, according to the embodiments herein.

FIG. 25 shows a graphical representation illustrating the effects of viability on the human liver carcinoma cell line in presence of silver nanoparticles, silver coated SPIONs, gold coated SPIONs and silver-gold coated SPIONs, according to the embodiments herein. With respect to FIG. 25, the silver nanoparticles exhibited significant toxicity at the highest applied concentration of 80 μg/ml. However, at the same particle concentration, both the silver coated SPIONs and the silver-gold coated SPIONs were fully compatible with the cells. The toxic effects of these engineered particles against bacteria together with their compatibility with human cells can introduce them as new "miracle nanoparticles" for fighting against antibacterial resistance threat.

In order to further investigate the effect of silver and silver coated SPIONs (SPION-silver core-shell nanoparticles) on the cell line (HepG2), the Transmission Electron Microscopy (TEM) method was utilized. The Transmission electron micrographs of HepG2 cells were taken after a 24 h of growth in tissue culture polystyrene wells in the presence of silver and silver coated SPIONs. The concentrations of the nanoparticles were exactly same.

Figure 26:
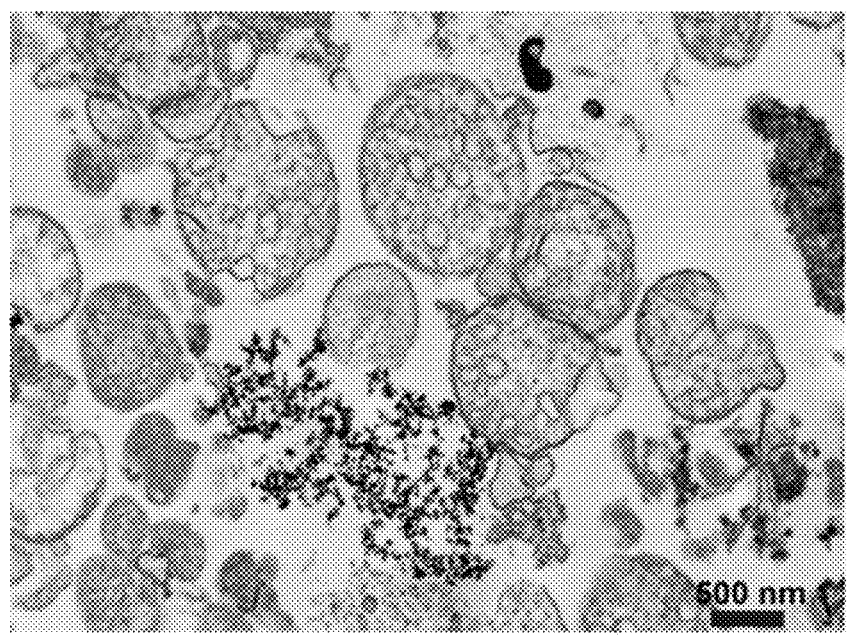
FIG. 26 shows a Transmission Electron Microscopy (TEM) image of the human liver carcinoma cell line in the presence of silver nanoparticles, according to an embodiment herein.

FIG. 26 shows a Transmission Electron Microscopy (TEM) image of the human liver carcinoma cell line in presence of silver nanoparticles, according to an embodiment herein. With respect to FIG. 26, the silver nanoparticles demonstrated an adverse effect on the HepG2 cells.

Figure 27:
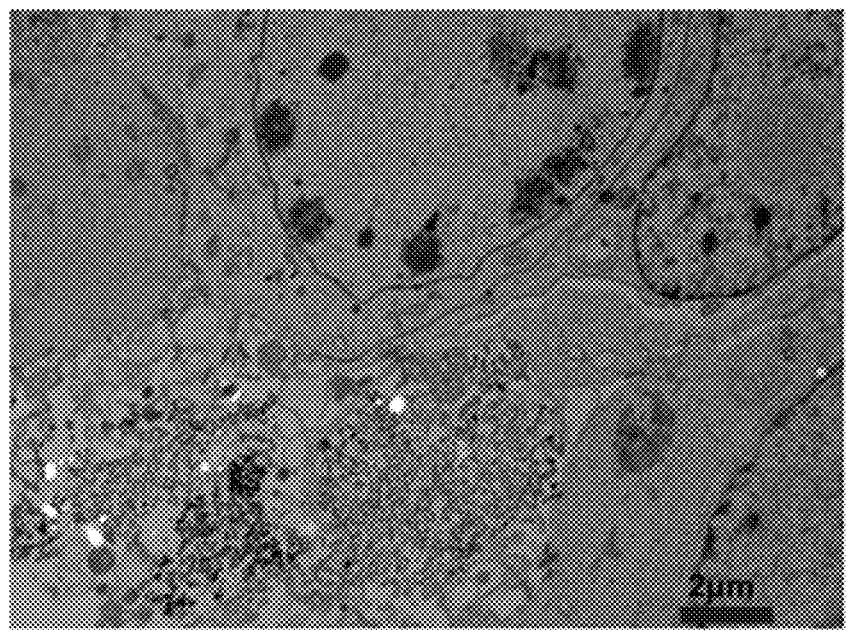
FIG. 27 shows a Transmission Electron Microscopy (TEM) image of the human liver carcinoma cell line in the presence of silver coated SPIONs, according to an embodiment herein.

FIG. 27 shows a Transmission Electron Microscopy (TEM) image of the human liver carcinoma cell line in presence of silver coated SPIONs, according to an embodiment herein. With respect to FIG. 27, the cells appeared normal in presence of silver coated SPIONs. Also as can be seen in the FIG. 27, the SPION-silver particles had entered into the intercellular environment via endocytosis process.

The TEM images confirm the toxic effects of the silver and the silver coated SPIONs on the cell lines. It was concluded that the silver particles had toxic effects on the cells while there was no sign of toxicity for silver coated SPIONs (i.e. the silver-SPIONs core shell particles).

The antibacterial activity of silver nano particles can be due to multiple mechanisms. The main mechanism suggested is related to the oxidative stress generated by Reactive Oxygen Species (ROS). Choi et al showed that silver nanoparticles with diameters lower than 5 nm could be more toxic to bacteria compared with the bigger ones. Similar effect can exist for the silver-ring coated nanoparticles. More specifically, these particles possess promising capability to induce oxidative stress generated by ROS.

Another possible antibacterial mechanism is the electrostatic interactions between nanoparticles and bacterial cell membranes or cell membrane proteins which can result in physical damage followed by bacteria death. Due to their different physicochemical properties in comparison with silver nanoparticles, the silver-ring coated nanoparticles induce different bacterial or cellular responses. It is now well recognized that once nanoparticles infiltrate the biological medium, their surfaces get covered by various proteins. The composition of the associated proteins in this coating is strongly dependent on the physicochemical properties of the nanoparticles. Therefore, the compositions of protein corona on the surface of silver-ring coated particles are completely different with that on the silver nanoparticles resulting in dual toxicity effects of these particles against bacteria and cells.

In order to confirm the mentioned mechanisms, an Electron Microscopy Analysis was conducted. The Electron Microscopy Analysis was conducted at the highest applied particle concentration. The highest applied particles concentration was silver metal ion concentration of 80 µg/ml at interaction time of 3 h with the human liver carcinoma cells.

Figure 28A:
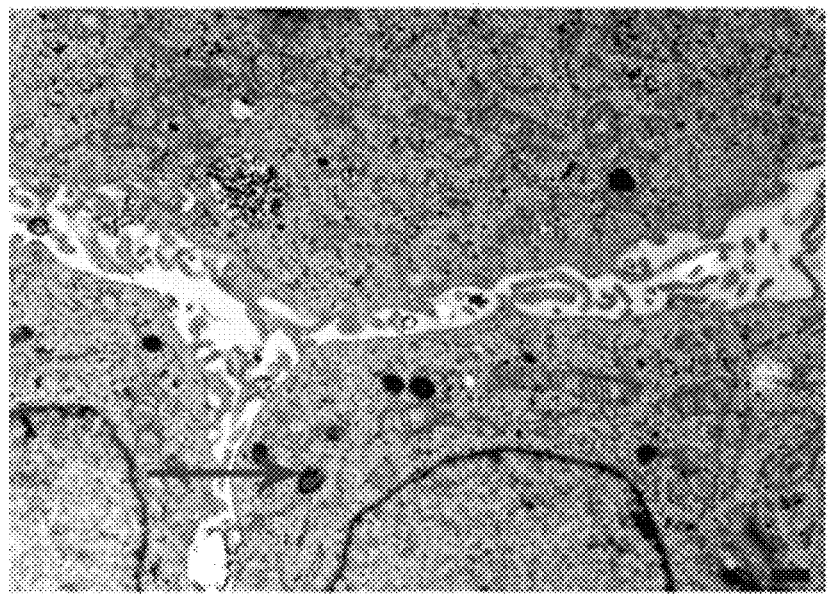
FIG. 28A shows a transmission electron microscopy (TEM) image of the accumulated silver nanoparticles in the human carcinoma liver cells, according to an embodiment herein.

FIG. 28A shows a transmission electron microscopy (TEM) image of the accumulated silver nanoparticles in the human carcinoma liver cells, according to an embodiment herein. With respect to FIG. 28A, the accumulation of the silver nanoparticles in the cells is clearly visible as shown by an arrow.

Figure 28B:
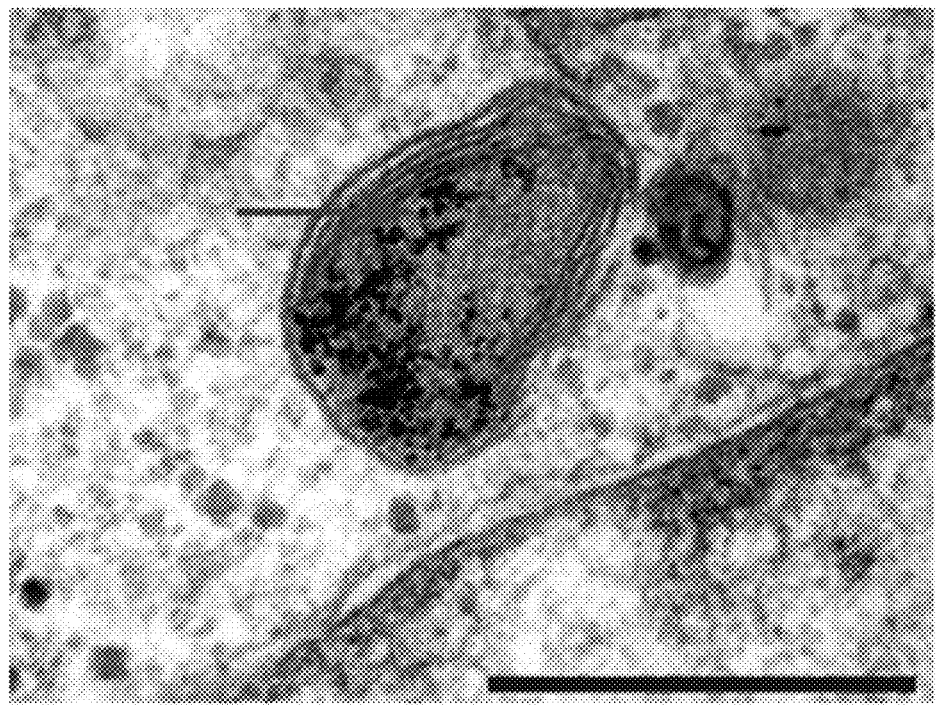
FIG. 28B shows a transmission electron microscopy (TEM) image of the accumulated silver nanoparticles in the mitochondria of the human carcinoma liver cell, according to an embodiment herein.
Figure 28C:
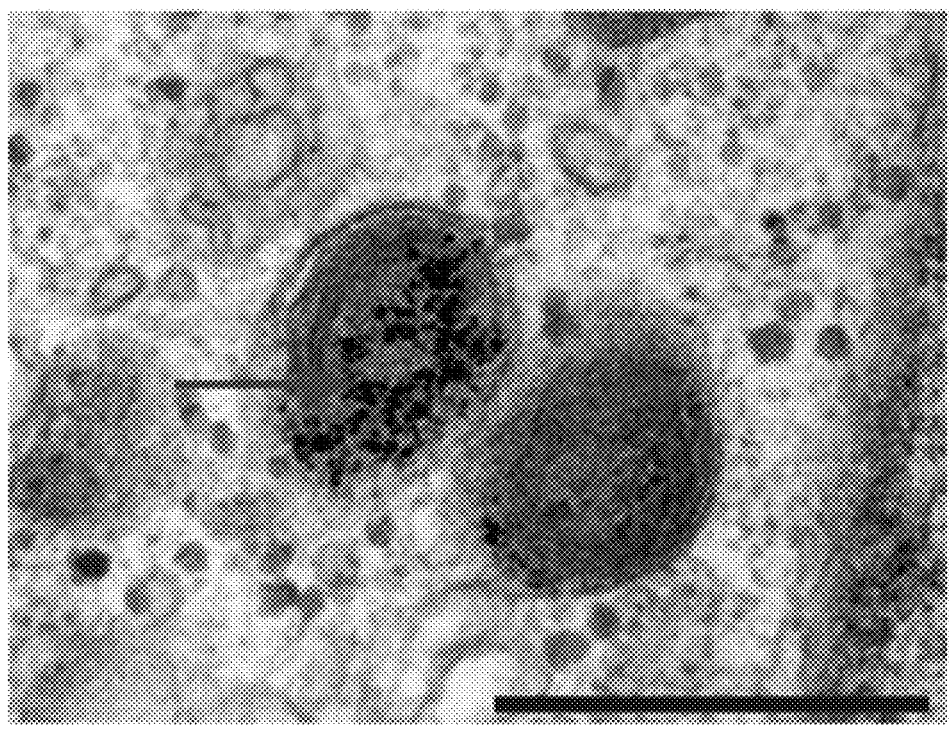
FIG. 28C shows a transmission electron microscopy (TEM) image of the accumulated silver nanoparticles in the mitochondria of another human carcinoma liver cell, according to an embodiment herein.

FIG. 28B shows a transmission electron microscopy (TEM) image of the accumulated silver nanoparticles in the mitochondria of the human carcinoma liver cell, according to an embodiment herein. FIG. 28C shows a transmission electron microscopy (TEM) image of the accumulated silver nanoparticles in the mitochondria of another human carcinoma liver cell, according to an embodiment herein. With respect to FIG. 28B and FIG. 28C, the accumulation of the silver nanoparticles in the mitochondria of the liver cells is clearly visible as shown by an arrow.

Figure 29A:
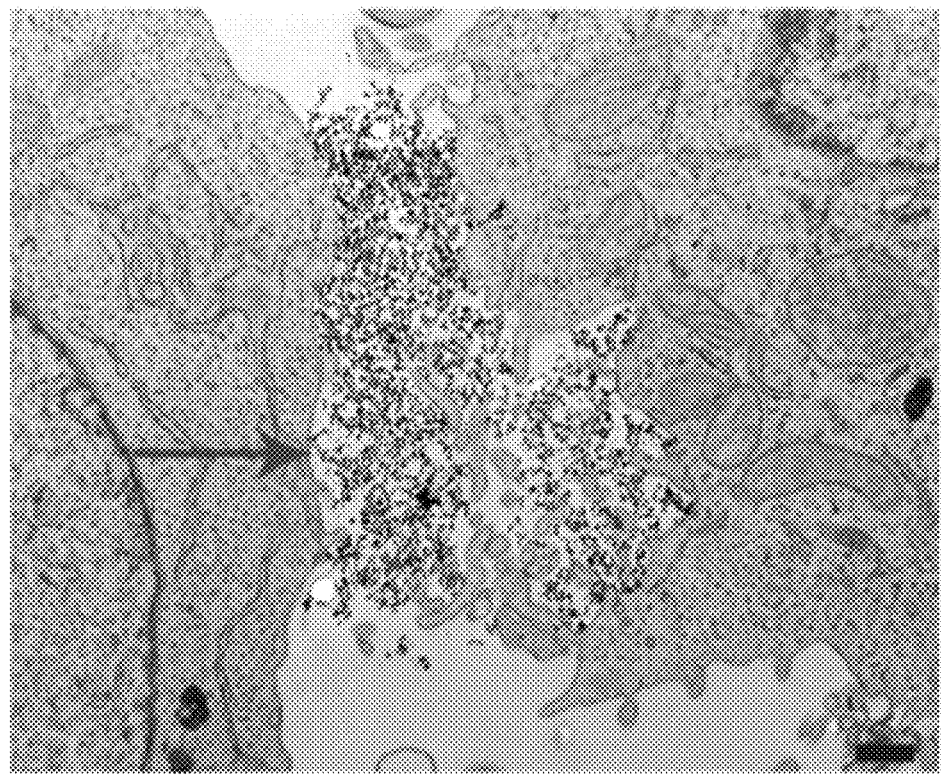
FIG. 29A shows a transmission electron microscopy image of the silver coated SPIONs in presence of the human carcinoma cells, according to an embodiment herein.

FIG. 29A shows a transmission electron microscopy image of the silver coated SPIONs in presence of the human carcinoma cells, according to an embodiment herein. With respect to FIG. 29A, the accumulation of the silver coated SPIONs in the outer region of cells is clearly visible as shown by an arrow.

Figure 29B:
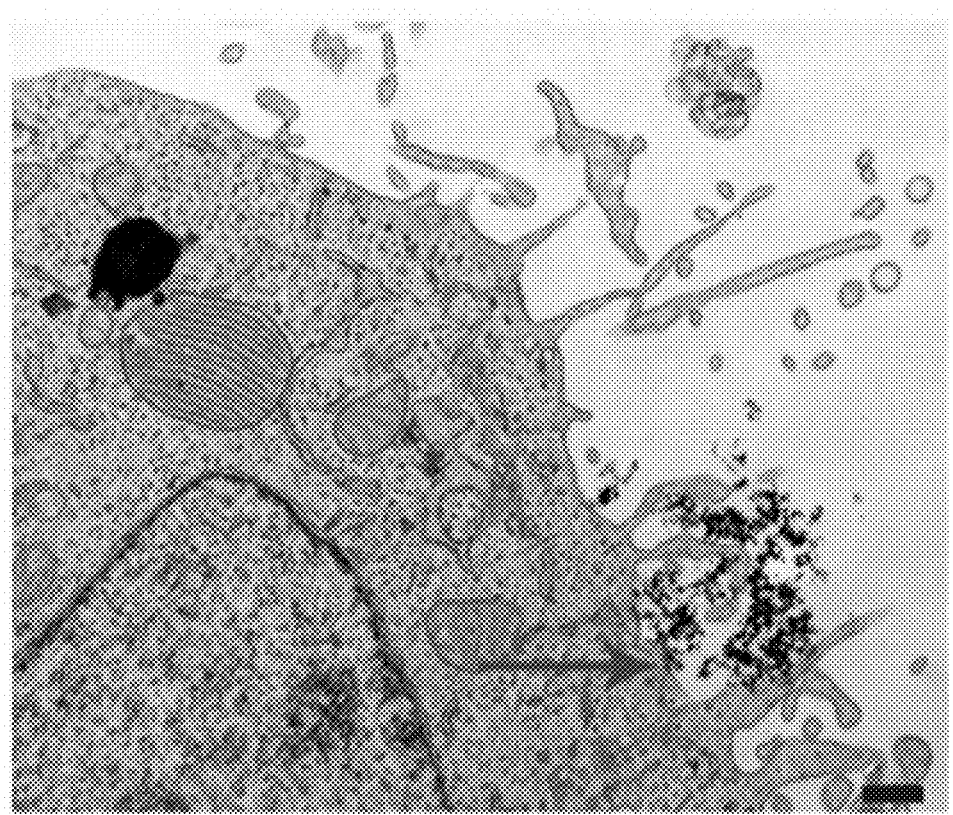
FIG. 29B shows a transmission electron microscopy (TEM) image of the accumulated silver coated SPIONs in the outer region of the human carcinoma liver cell, according to an embodiment herein.

FIG. 29B shows a transmission electron microscopy (TEM) image of the accumulated silver coated SPIONs in the outer region of the human carcinoma liver cell, according to an embodiment herein. With respect to FIG. 29B the accumulated silver coated SPIONs on the outer regions of the cells is clearly visible.

Figure 29C:
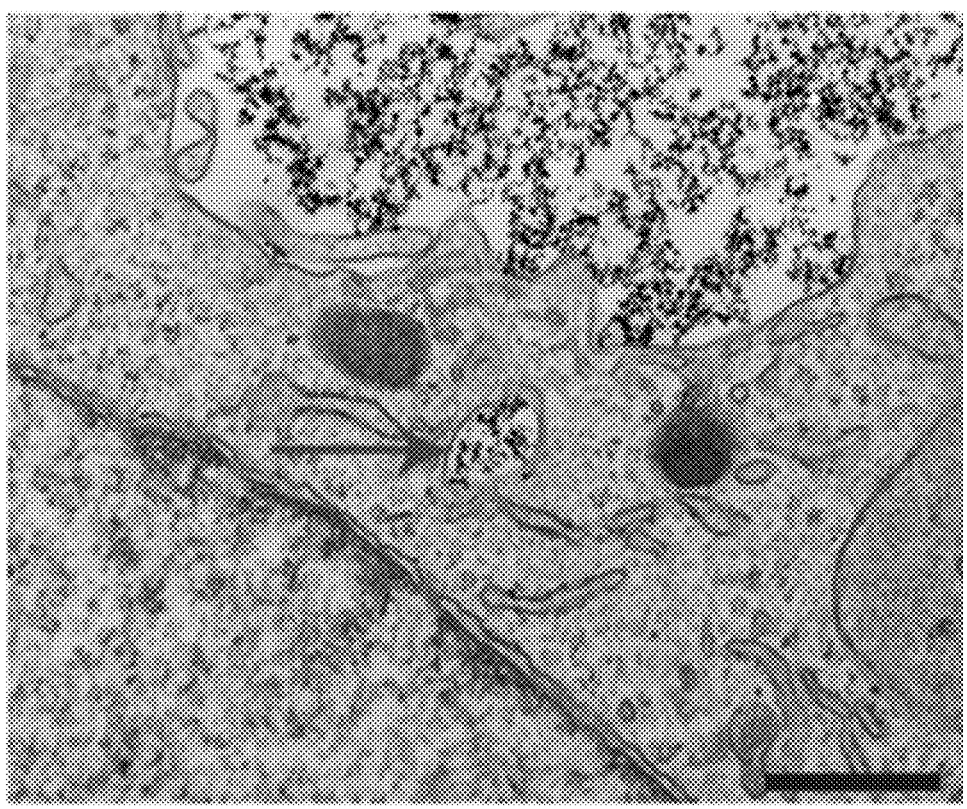
FIG. 29C shows a transmission electron microscopy (TEM) image of the accumulated silver nanoparticles inside the human carcinoma liver cell, according to an embodiment herein.

FIG. 29C shows a transmission electron microscopy (TEM) image of the accumulated silver nanoparticles inside the human carcinoma liver cell, according to an embodiment herein. With respect to FIG. 29C, the silver coated SPIONs have entered the cell cytoplasm due to the process of endocytosis, but the silver coated SPIONs have not entered the mitochondria of the cells thus proving the non-toxic effects of the silver coated SPIONs on the cells as compared to the silver nanoparticles as can be seen from FIGS. 28A, 28B and 28C.

Thus, the results confirmed the accumulation of silver nanoparticles in mitochondria of the cells. As proposed before, the most possible mechanism of toxicity of silver nanoparticles is their capability for disruption of the mitochondrial respiratory chain leading to a production of Reactive Oxygen Species (ROS) and the interruption of ATP synthesis. This in turn causes DNA damage. In contrast, the silver coated SPIONs entered the intercellular medium via endocytosis uptake and there is no trace of particles in the mitochondria of the cells. Thus, there were no or little amounts of ROS production resulting in no or reversible damage to the DNA.

Thus, the embodiments herein provide a new class of engineered multimodal nanoparticles comprising a magnetic core and a silver ring with a polymeric gap. The results indicated promising capability of the designed multimodal nanoparticles for high-yield antibacterial effects and eradication of bacterial biofilms while the particles were completely compatible with the cells. Utilizing a gold ring as an intermediate coating on the produced nanoparticles may exploit new opportunities for theranosis applications. However such innovative prospects will require significant consideration by scientific community in the future. The silver-ring engineered magnetic nanoparticles are promising antimicrobial agents that can be used to treat infectious diseases. These nano particulate systems can be improved in future inorder to avoid antibiotic resistance owing to their multi-antibiotic capabilities with extensive changeable physicochemical properties.

The formation of these nanoparticles strongly enhances the antimicrobial activities of silver not only through up regulation of ROS production in bacteria but also by the deep penetration of the particles within the bacterial biofilm using an external magnetic field. The engineered magnetic nanoparticles do not cause toxicity to the human cells provides an efficient antimicrobial agent in treating pathogens and infections. The prospective applications of antibacterial silver-ring SPIONs will require significant consideration by scientific community in the near future.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. An engineered multimodal nanoparticle with anti-bacterial effect and theranosis application comprises:
   a super paramagnetic iron oxide nanoparticle (SPION) with a plurality of metallic coatings and a plurality of polymeric gaps, and wherein one gap is made up of a plurality of polymeric molecules, wherein the coating has a thickness of 2-3 nm, and wherein the plurality of polymeric molecules is selected from a group consisting of carboxylated-dextran compound, ethandiyl bis(isonicotinate) compound, bis 2-((4-pyridinyl carbonyl)oxy)ethyl disulfide compound, poly-L-histidine compound and a combination thereof, and wherein the polymeric gap has a thickness of 3-5 nm, and wherein the nanoparticle has antibacterial property, wherein the nanoparticle stops a growth of a bacterial biofilm, wherein the nanoparticle is compatible with biological cells, and wherein the nanoparticle has Surface Enhanced Raman Scattering (SERS) properties.

2. The nanoparticle according to claim 1, wherein the metal is selected from a group consisting of a silver, a gold and a combination thereof.

3. The nanoparticle according to claim 1, wherein the coating is two in number.

4. The nanoparticle according to claim 1, wherein the gap is two in number.

5. A method of synthesizing an engineered multimodal nanoparticle with antibacterial effect and theranosis application comprising the steps of:
   mixing a solution of SPIONs with a solution of a polysaccharide at room temperature for a predetermined time to obtain SPIONs with a coating of the polysaccharide, wherein the predetermined time is 72 hours;
   mixing the obtained SPIONs with a solution of a preset compound for a preset time period to obtain SPIONs with a further coating of the preset compound and wherein the preset compound is ethanediyl bis(isonicotinate) and wherein the preset time period is 20 minutes;
   mixing the obtained SPIONs with a metal salt solution for a given time duration to obtain SPIONs with an accumulated metal ions on surface and wherein the metal salt solution is silver nitride solution and wherein the given time duration is 20 minutes;
   separating the obtained SPIONs from the metal salt solution;
   reducing the obtained SPIONs by adding a reducing agent to obtain SPIONs with a metal coating on an outer surface having a polymeric gap, wherein the polymeric gap is situated in between the metal coating and the SPION surface, wherein the reducing agent is sodium borohydride; and
   collecting the obtained SPIONs.

6. The method according to claim 5, wherein the metal coating is a silver coating and wherein the metal coating has a thickness of 2-3 nm.

7. The method according to claim 5, wherein the polysaccharide is carboxylated dextran.

8. The method according to claim 5, wherein the polymeric gap is made up of molecules of a carboxylated dextran and molecules of an ethanediyl bis(isonicotinate) and wherein the polymeric gap has a thickness of 3-5 nm.

9. A method of synthesizing an engineered multimodal nanoparticle with anti- bacterial effect and theranosis application comprising the steps of:
   dispersing a gold coated SPIONs in a solution of a disulphide compound, wherein the disulphide compound is bis 2-((4-pyridinylcarbonyl)oxy)ethyl disulfide;
   mixing the solution for a preset time duration, wherein the preset time duration is 5 hrs;
   collecting the gold coated SPIONs;
   mixing the collected gold coated SPIONs with a salt solution, wherein the salt solution is silver nitride solution;
   adding a reducing agent to obtain a SPIONs with a plurality of metallic coatings and a plurality of polymeric gaps, wherein the reducing agent is sodium borohydride.

10. The method according to claim 9, wherein the metallic coatings are two in number and wherein the metallic coating has a thickness of 2-3 nm.

11. The method according to claim 9, wherein the metallic coatings include a gold coating and a silver coating.

12. The method according to claim 9, wherein the polymeric gaps are two in number and wherein the polymeric gaps have a thickness of 3-5 nm.

13. The method according to claim 9, wherein the polymeric gaps are made up of a plurality of molecules of polymers, and wherein the polymers are selected from a group consisting of carboxylated-dextran, ethanediyl bis(isonicotinate), bis 2((4-pyridinylcarbonyl)oxy)ethyl disulfide, poly-L histidine and a combination thereof.

* * * * *